(12) United States Patent
Chen et al.

(10) Patent No.: US 10,500,203 B2
(45) Date of Patent: Dec. 10, 2019

(54) COMPOSITIONS AND METHODS FOR TREATING BONE DISEASES

(71) Applicant: RUSH UNIVERSITY MEDICAL CENTER, Chicago, IL (US)

(72) Inventors: Di Chen, Chicago, IL (US); Rong Xie, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 15/758,083

(22) PCT Filed: Aug. 23, 2016

(86) PCT No.: PCT/US2016/048118
§ 371 (c)(1),
(2) Date: Mar. 7, 2018

(87) PCT Pub. No.: WO2017/044302
PCT Pub. Date: Mar. 16, 2017

(65) Prior Publication Data
US 2018/0243305 A1 Aug. 30, 2018

Related U.S. Application Data

(60) Provisional application No. 62/215,987, filed on Sep. 9, 2015.

(51) Int. Cl.
| | |
|---|---|
| *A61K 31/519* | (2006.01) |
| *A01K 67/027* | (2006.01) |
| *A61P 19/08* | (2006.01) |
| *A61K 9/00* | (2006.01) |
| *A61K 31/4439* | (2006.01) |
| *A61K 31/506* | (2006.01) |
| *A61K 31/52* | (2006.01) |
| *A61K 49/00* | (2006.01) |

(52) U.S. Cl.
CPC ........ *A61K 31/519* (2013.01); *A01K 67/0276* (2013.01); *A61K 9/0034* (2013.01); *A61K 31/4439* (2013.01); *A61K 31/506* (2013.01); *A61K 31/52* (2013.01); *A61P 19/08* (2018.01); *A01K 2217/075* (2013.01); *A01K 2217/077* (2013.01); *A01K 2227/105* (2013.01); *A01K 2267/0306* (2013.01); *A61K 49/0008* (2013.01); *A61K 2123/00* (2013.01)

(58) Field of Classification Search
USPC ..................................................... 514/259.3
See application file for complete search history.

(56) References Cited

U.S. PATENT DOCUMENTS

| | | |
|---|---|---|
| 2011/0289605 A1 | 11/2011 | Chen |
| 2013/0280233 A1 | 10/2013 | Kahn et al. |
| 2014/0199399 A1 | 7/2014 | Streisand et al. |
| 2015/0010515 A1 | 1/2015 | Schoeler et al. |
| 2016/0122711 A1* | 5/2016 | Semechkin ............ A61K 35/30 424/93.7 |

FOREIGN PATENT DOCUMENTS

EP        2270229        1/2011

OTHER PUBLICATIONS

Chung (Bone (2013) 52:651-658). (Year: 2013).*
Paley (J. Child. Orthop. (2016) 10:529-555). (Year: 2016).*
International Search Report and Written Opinion for PCT/US16/48118 dated Oct. 31, 2016, 9 pgs.
(Chung, R et al.) Roles of Wnt/beta-Catenin Signalling Pathway in the Bony Repair of Injured Growth Plate Cartilage in Young Rats. Bone. 2013. vol. 52; p. 651, first column, first paragraph, second column, first paragraph; p. 652, first column, second-fourth paragraphs; p. 656, second column, third paragraph; p. 657, second column, third paragraph.
(Boden, SD et al.) Proximal Femoral Focal Deficiency. Evidence for a Defect in Proliferation and Maturation of Chondrocytes. Journal of Bone and Joint Surgery. 1989. vol. 71, No. 8; pp. 1119-1129; abstract.
(Watanabe, K et al.) Winning WNT: Race to Wnt Signaling Inhibitors. Proceedings of National Academy of Science. 2011. vol. 108, No. 15; p. 5929, first column, second-third paragraphs, second column, first paragraph; figure 1.
(Xie, R et al.) Generation of Axin1 Conditional Mutant Mice. Genesis. 2011. vol. 49, No. 2; pp. 98-102 (pp. 1-7); p. 3, second paragraph.
(Dao, Dy et al.) Axin2 Regulates Chondrocyte Maturation and Axial Skeletal Development. Journal of Orthopedic Research. 2010. vol. 28, No. 1; pp. 89-95 (pp. 1-12); p. 2, fourth paragraph.
(Ouyang, Z et al.) Prx1 and 3.2 kb Col1a1 Promoters Target Distinct Bone Cell Populations in Transgenic Mice. Bone. Apr. 2015; pp. 136-145 (pp. 1-22); p. 3, second paragraph; p. 7, third paragraph.
Achterman C, and Kalamchi A (1979) Congenital deficiency of the fibula. J Bone Joint Surg [Br] 61:133-7.
Brunet, LJ, McMahon JA, McMahon AP, and Harland RM (1998) Noggin, cartilage morphogenesis, and joint formation in the mammalian skeleton. Science 280:1455-1457.
Coventry MB, and Johnson EW (1952) Congenital absence of fibula. J Bone Joint Surgery [Am] 34:941-55.
Chia IV, and Costantini F (2005) Mouse axin and axin2/conductin proteins are functionally equivalent in vivo. Mol Cell Biol 25: 4371-4376.
Chia IV, Kim MJ, Itoh K, Sokol SY, and Costantini F (2009) Both the RGS domain and the six C-terminal amino acids of mouse Axin are required for normal embryogenesis. Genetics 181:1359-1368.
Farley FW, Soriano P, Steffen LS, and Dymecki SM (2000) Widespread recombinase expression using FLPeR (Flipper) mice. Genesis 28:106-110.

(Continued)

*Primary Examiner* — Marcos L Sznaidman
(74) *Attorney, Agent, or Firm* — Brinks Gilson & Lione

(57) ABSTRACT

Certain aspects of the present invention generally relate to compositions and methods for treating a bone disease, for example a genetic bone disease. In one embodiment the bone disease is fibular hemimelia, proximal femoral focal deficiency, tarsal coalition or humeroradial synostosis.

13 Claims, 29 Drawing Sheets

(56) References Cited

OTHER PUBLICATIONS

Florio I, Wisser J, Huch R, and Huch A (1999) Prenatal ultrasound diagnosis of a femur-fibula-ulna complex during the first half of pregnancy. Fetal Diagn Ther 14:310-312.
Logan M, Martin JF, Nagy A, Lobe C, Olson EN, and Tabin CJ (2002) Expression of Cre Recombinase in the developing mouse limb bud driven by a Prxl enhancer. Genesis 33:77-80.
Gillespie R, Torode IP. 1983. Classification and management of congenital abnormalities of the femur. J Bone Joint Surg (Br) 65( 557-68).
Gonsalves, F.C., Klein, K., Carson,B.B., Katz, S., Ekas,L.A., Evans, S., Nagourney, R., Cardozo,T., Brown, A.M., DasGupta, R. 2011. An RNAi-based chemical genetic screen identifies three small-molecule inhibitors of the Wnt/wingless signaling pathway. Proc Natl Acad Sci USA 108: 5954-5963.
Kulik SA, Jr., Clanton TO. 1996. Tarsal coalition. Foot & Ankle International 17(5): 286-96.
Ovchinnikov DA, Deng JM, Ogunrinu G, and Behringer RR (2000) Col2a1-directed expression of Cre recombinase in differentiating chondrocytes in transgenic mice. Genesis 26:145-146.
McIntyre JD, Benson MK. 2002. An aetiological classification for developmental Synostoses at the elbow. J Pediatr Orthop B. 11(4):313-319.
Perry WL III, Vasicek TJ, Lee JJ, Rossi JM, Zeng L, Zhang T, Tilghman SM, and Costantini F (1995) Phenotypic and molecular analysis of a transgenic insertional allele of the mouse Fused locus. Genetics141:321-332.
Rodda, SJ and McMahon AP (2006) Distinct roles for Hedgehog and canonical Wnt signaling in specification, differentiation and maintenance of osteoblast progenitors. Development 133:3231-3244.

Stanitski DF, and Stanitski CL (2003) Fibular hemimelia: A new classification system. J Pediatr Orthop 23: 30-34.
Thompson TC, Straub LR, and Arnold WD (1957) Congenital absence of the fibula. J Bone Joint Surg 39A, 1229-1237.
Tsumaki N, Tanaka K, Arikawa-Hirasawa E, Nakase T, Kimura T, Thomas JT, Ochi T, Luyten FP, and Yamada Y (1999) Role of CDMP-1 in skeletal morphogenesis: Promotion of mesenchymal cell recruitment and chondrocyte differentiation. J Cell Biol 144:161-173.
Xie R, Jiang R, and Chen D (2011) Generation of Axin1 conditional mutant mice. Genesis 9:98-102.
Yan Y, Tang D, Chen M, Huang J, Xie R, Jonason JH, Tan X, Hou W, Reynolds D, Hsu W, Harris SE, Puzas JE, Awad H, O'Keefe RJ, Boyce BF, and Chen D (2009) Axin2 controls bone remodeling through the {beta}-catenin-BMP signaling pathway in adult mice. J Cell Sci 122: 3566-3578.
Yu HM, Jerchow B, Sheu TJ, Liu B, Costantini F, Puzas JE, Birchmeier W, and Hsu W (2005) The role of Axin2 in calvarial morphogenesis and craniosynostosis. Development 132:1995-2005.
Yu PB, Hong CC, Sachidanandan C, Babitt JL, Deng DY, Hoyng SA, Lin HY, Bloch KD, and Peterson RT (2008) Dorsomorphin inhibits BMP signals required for embryogenesis and iron metabolism. Nat Chem Biol 4:33-41.
Zeng L, Fagotto F, Zhang T, Hsu W, Vasicek TJ, Perry WL 3rd, Lee JJ, Tilghman SM, Gumbiner BM, and Costantini F (1997) the mouse Fused locus encodes Axin, an inhibitor of the Wnt signaling pathway that regulates embryonic axis formation. Cell 90:181-92.
Zou H, Wieser R, Massague J, and Niswander L (1997) Distinct roles of type I bone morphogenetic protein receptors in the formation and differentiation of cartilage. Genes Dev 11:2191-2203.

* cited by examiner

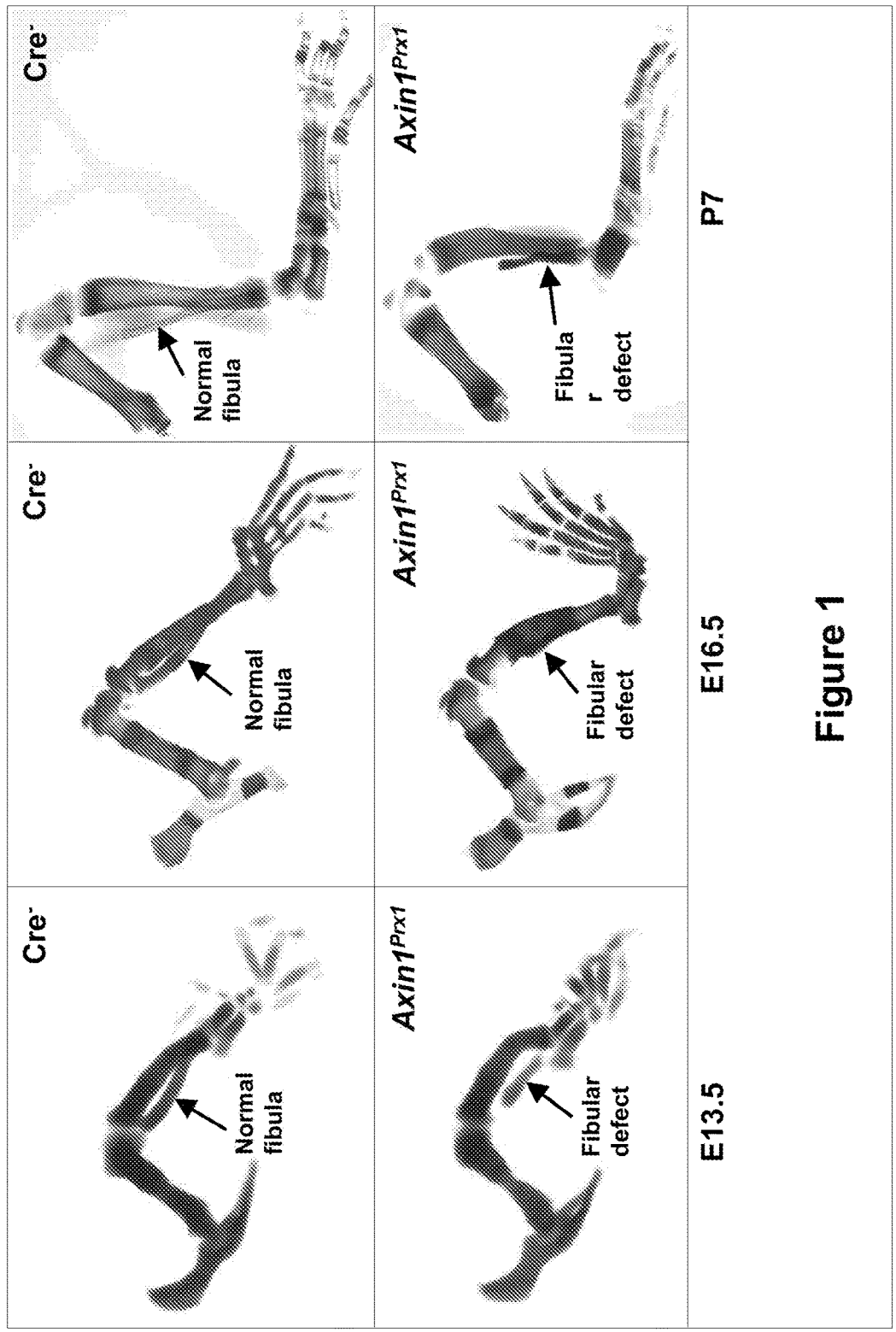

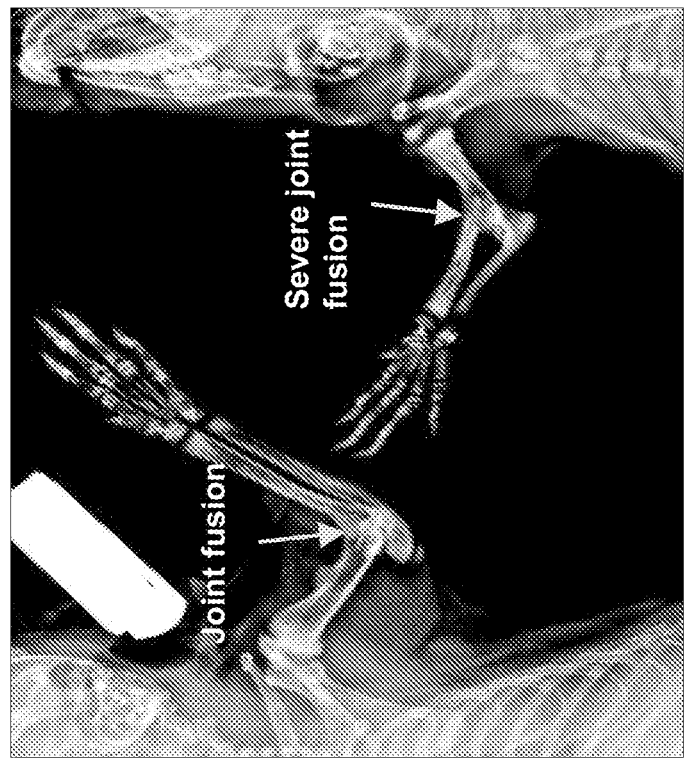
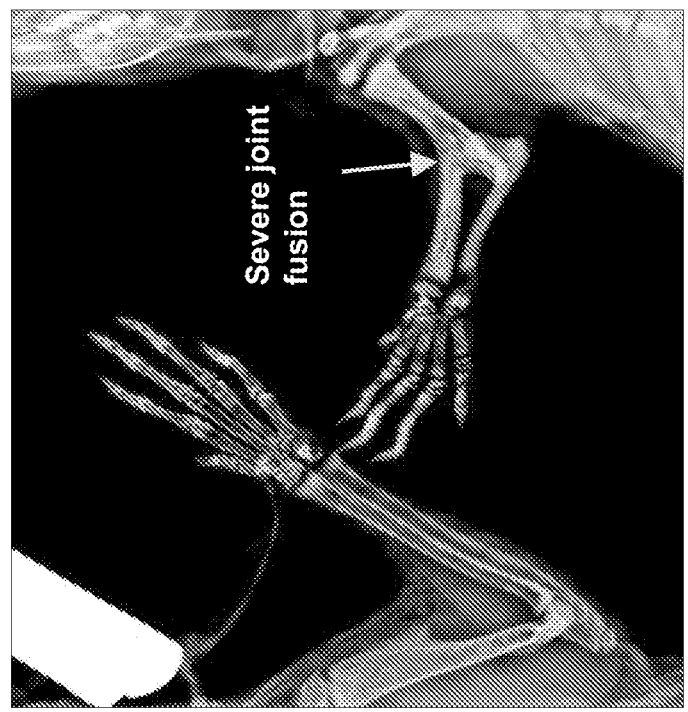
Figure 11

1) 1st distal carpal  C) Centrale
2) 2nd distal carpal  U) Ulnare
3) 3rd distal carpal  P) Pisiform
4/5) 4th & 5th distal carpal  Ul) ulnar sesamoid
R) Fused radiale and intermedium

COMPOSITIONS AND METHODS FOR TREATING BONE DISEASES

CROSS-REFERENCE TO RELATED APPLICATIONS

This application is a National Stage of PCT/US2016/048118, filed Aug. 23, 2016, which claims the benefit of the filing date of U.S. Provisional Patent Application No. 62/215,987, filed Sep. 9, 2015, the contents of which applications are hereby incorporated by reference.

TECHNICAL FIELD

The present invention generally relates to compositions and methods for treating a bone disease, for example a genetic bone disease. In one embodiment, the bone disease is fibular hemimelia, proximal femoral focal deficiency, tarsal coalition or humeroradial synostosis.

BACKGROUND

Fibular hemimelia (FH) is a disease of congenital limb deficiency characterized by the partial or total absence of the fibula. It represents the most common deficiency of long bones. The cause of FH disease remains unknown. It was first described by Gollier in 1698 (Coventry and Johnson, 1952). It has been estimated that there is approximately 1 in 50,000 cases live births (Florio et al., 1999). FH exhibits as a clinical spectrum from partial absence to complete absence of the fibular bone (Achterman and Kalamchi, 1979). The appearance of the developmental anomaly is not only absence of the fibula but also as follows: the femur is short, the tibia is bowed, the foot is deformed in an equinovalgus position, and presents tarsal coalition. Absence of lateral rays of the foot may be seen in patients with severe FH disease.

Proximal femoral focal deficiency (PFFD) is a rare congenital anomaly characterized by abnormal development of the proximal femur (Gillespie et al., 1983). Symptoms range from an absence of the entire femur and abnormal development of the pelvis to a hypoplastic femur of normal configuration. The disorder is unilateral in 90% of the cases. It is commonly linked with the absence or shortening of leg bone and the absence of a kneecap. The lower extremity is abducted, flexed and externally rotated through the upper femur. Other features of PFFD include the dislocation or instability of the joint between the femur and the kneecap, a shortened tibia or fibula, and foot deformities.

Tarsal coalition (TC) is a fibrous, cartilaginous, or bony connection of two or more tarsal bones. Foot pain is the typical symptom. Although usually developing during adolescence, the onset of aching pain in the foot tends to correlate with age at which the coalition bar ossifies (Kulik et al., 1996). Classic presenting symptoms are that the peroneal spastic flat foot, with the hindfoot held in eversion and spasm of the peroneals noted on attempts to invert the foot. The most common tarsal coalitions involve the calca-neonavicular and talocalcaneal joints.

Humeroradial synostosis (HRS) is rare congenital abnormality in which there is fusion between humerus and radius. HRS is categorized by deformity. Class I is associated with ulnar ray hypoplasia and elbow extension. Class II synostoses are not associated with hypolasia where the elbow is flexed (McIntyre et al., 2002). HRS often causes little functional disability. Both sporadic and genetic cases of humeroradial synostosis are encountered.

The etiology of fibular hemimelia (FH), proximal femoral focal deficiency (PFFD), tarsal coalition (TC) and humeroradial synostosis (HRS) disease are unclear, but genetic and environmental factors are generally acknowledged. Understanding the pathological mechanisms of these diseases will help the prevention and treatment of the diseases.

SUMMARY OF THE PREFERRED EMBODIMENTS

One aspect of the present invention provides a method for treating a genetic bone disease present in a subject. In one embodiment, the method includes administering to a subject in need of such treatment a composition comprising a therapeutically effective amount of an inhibitor of beta-catenin signaling. The disease may be, for example, fibular hemimelia (FH), proximal femoral focal deficiency (PFFD), tarsal coalition (TC) or humeroradial synostosis (HRS).

The composition may be administered in-utero and/or after birth of the subject. For example, the composition may be administered in the third trimester of pregnancy. The subject may be a subject having an elevated level of beta-catenin signaling. In certain embodiments, the inhibitor of beta-catenin signaling is LGK-974, IWP-2, iCRT3, iCRT 14, ICG 001, XAV-939, KY02111, or a combination of at least two of these compounds.

Another aspect of the invention provides a method for treating an orthopedic disease, including administering to a subject in need of such treatment a composition including a therapeutically effective amount of an inhibitor of bone morphogenetic protein (BMP) signaling. The disease may be, for example, fibular hemimelia (FH), proximal femoral focal deficiency (PFFD), tarsal coalition (TC) or humeroradial synostosis (HRS).

The composition may be administered in-utero and/or after birth of the subject. For example, the composition may be administered in the third trimester of pregnancy. The subject may be a subject having an elevated level of BMP signaling. In certain embodiments, the inhibitor of BMP signaling dorsomorphin dihydrochloride, K 02288, DMH-1, LDN 193189 trihydrochloride or a combination of at least two of these compounds.

Another aspect of the invention provides a method for identifying compounds for treating a genetic orthopedic disease. In one embodiment, the method includes administering a test compound to an Axin1$^{Prx1}$ mouse embryo and examining an elbow joint of the embryo to determine the extent of separation of humerus, radius and ulna. Compounds that exhibit at least a predetermined separation of the humerus, radius and ulna are identified as compounds for treating the genetic orthopedic disease. In one embodiment, the examination is by x-ray analysis.

BRIEF DESCRIPTION OF THE DRAWINGS

FIG. 1 shows defects in fibular development were observed in Axin1$^{Prx1}$ conditional KO embryos and postnatal mice. Alizerin red/Alcian blue staining was performed using hind limbs of E13.5 and 16.5 embryos and P7 postnatal mice. Axin1$^{Prx1}$ KO embryos and mice showed partial development of fibula. Cre-embryos (controls) showed mineralization of fibula at E16.5 or P7 stages. In contrast, the partially developed fibula of Axin1$^{Prx1}$ KO embryo and mouse did not mineralize even at day 7 of postnatal stage.

FIG. 11 shows Axin1$^{Prx1}$/Axin2$^{+/-}$ double KO mice having severe defects in joint fusion in forelimb. X-ray of forelimbs of 3-week-old (Axin1$^{flox/+}$)$^{Prx1}$/Axin2$^{+/-}$ (same as Cre-negative control mice), Axin1$^{Prx1}$ KO and Axin1$^{Prx1}$/Axin2$^{+/-}$ double KO mice were analyzed. More severe elbow joint fusion was observed in Axin1$^{Prx1}$/Axin2$^{+/-}$ mice. Arrows indicate the fusion of humerus and radius in Axin1$^{Prx1}$ KO mice and Axin1$^{Prx1}$/Axin2$^{+/-}$ double KO mice.

DETAILED DESCRIPTION OF THE PREFERRED EMBODIMENTS

Definitions

Figure 2A:
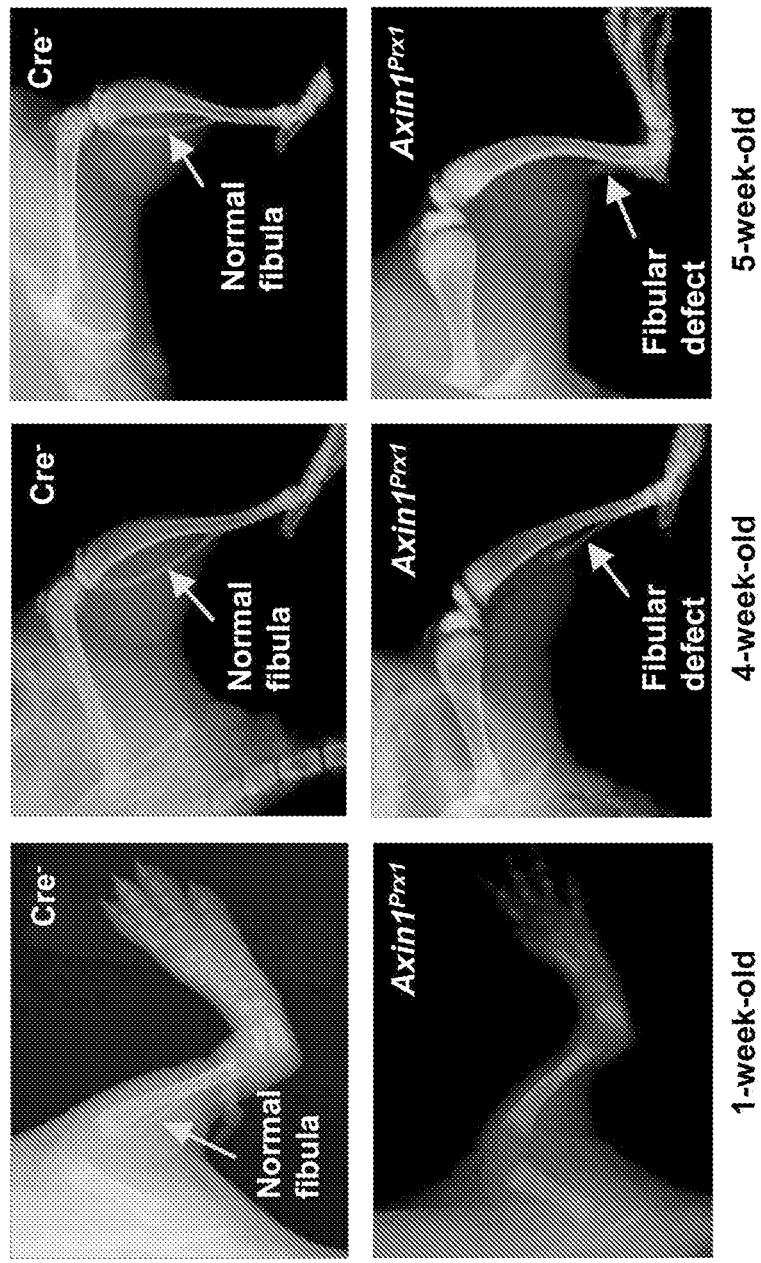
FIG. 2(a) shows defects in fibular development were observed in Axin1$^{Prx1}$ conditional KO mice. 52 Axin1$^{Prx1}$ KO mice were generated and all of them showed defects in fibular development. Radiographic analysis showed that the absence of the fibula in some of Axin1$^{Prx1}$ mice was complete (1-week-old, lower panel) or almost complete (>50% loss, 27/52) where only a distal, vestigial fragment was present (5-week-old, tower panels). The other Axin1$^{Prx1}$ mice had partial absence of the fibula (30-50% loss, 23/52) (4-week-old, lower panel) in which the proximal portion of the fibula was absent while the distal portion was present but could not support the ankle.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The term "therapeutic effect" as used herein means an effect which induces, ameliorates or otherwise causes an improvement in the pathological symptoms, disease progression or physiological conditions associated with or resistance to succumbing to a disorder, for example a genetic bone disease, of a human or veterinary subject. The term "therapeutically effective amount" as used with respect to a drug means an amount of the drug which imparts a therapeutic effect to the human or veterinary subject. The therapeutically effective amount may be delivered to the subject in-utero (before birth) and after the birth of the subject.

Methods for Treating a Genetic Bone Disease

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of methods, methods of analysis, or other aspects, are disclosed. It is to be understood that each such disclosed feature or features can be combined with the generalized features discussed, to form a disclosed embodiment of the present invention.

Axin1 is a critical negative regulator of the canonical Wnt-signaling pathway. It is a concentration-limiting factor in the β-catenin degradation complex. Axin1 null mutant mouse embryos typically die at embryonic day 9.5, precluding direct genetic analysis of the roles of Axin1 in many developmental and physiological processes using these mutant mice. Mice may be generated carrying two directly repeated loxP sites flanking the exon 2 region of the Axin1 gene. Such floxed-allele-carrying mice (Axin1$^{flox/flox}$) mice appear normal and fertile. Upon crossing the Axin1$^{flox/flox}$ mice to the CMV-Cre transgenic mice to generate Axin1$^{Prx1}$ mice, the loxP-flanked exon 2 region that encodes the N-terminus and the conserved regulation of G-protein signaling domain is efficiently deleted by Cre-mediated excision in vivo. Mouse embryos homozygous for the Cre/loxP-mediated deletion of exon 2 of the Axin1 gene display embryonic lethality and developmental defects similar to those reported for Axin1$^{-/-}$ mice. This Axin1$^{flox/flox}$ mouse model provides a valuable for systematic tissue-specific dissection of the roles of Axin1 in embryonic and postnatal development and diseases.

The present inventors have found that deletion of Axin1 in limb mesenchymal progenitor cells, through generating Axin1$^{Prx1}$ conditional knockout mice and Axin1$^{Prx1}$/Axin2$^{+/-}$ double KO mice, led to phenotypes assembling to specific genetic orthopaedic diseases, for example, fibular hemimelia (FH), proximal femoral focal deficiency (PFFD), tarsal coalition (TC) or humeroradial synostosis (HRS). They have found that Beta-catenin signaling is activated in Axin1$^{Prx1}$ conditional knockout mice and that deletion of one allele of β-catenin gene reverses disease phenotypes. Furthermore, inhibition of Wnt signaling using chemical inhibitors significantly reversed disease phenotypes of Axin1$^{Prx1}$ conditional KO mice. This provides evidence that inhibition of β-catenin is a potential treatment for these genetic orthopaedic diseases.

In addition, bone morphogenetic protein ("BMP") signaling is up-regulated in Axin1$^{Prx1}$ conditional knockout mice. Inhibition of BMP signaling using chemical inhibitor of BMP signaling also reversed disease phenotypes of Axin1$^{Prx1}$ conditional knockout mice, demonstrating that this specific BMP signaling inhibitor may be used to treat the diseases of such genetic bone diseases.

One aspect of the present invention provides a method for treating a subject having a genetic bone disease. In one embodiment, the method includes administering a composition including a therapeutically effective amount of an inhibitor of beta-catenin signaling. The disease may be, for example, fibular hemimelia (FH), proximal femoral focal deficiency (PFFD), tarsal coalition (TC) or humeroradial synostosis (HRS).

The composition may be administered in-utero and/or after birth of the subject. For example, when the subject is a human fetus, the composition may be administered in the first, second or third trimester of development. The subject may be a subject having an elevated level of β-catenin signaling. In certain embodiments, the level of β-catenin signaling is determined and the treatment administered on the basis of this level.

In certain embodiments, the inhibitor of beta-catenin signaling is LGK-974 ([2,4'-Bipyridine]-5-acetamide, 2',3-dimethyl-N-[5-(2-pyrazinyl)-2-pyridinyl]-), IWP-2 (Acetamide, N-(6-methyl-2-benzothiazolyl)-2-[(3,4,6,7-tetrahydro-4-oxo-3-phenylthieno[3,2-d]pyrimidin-2-yl)thio], iCRT3 (2-[[[2-(4-ethylphenyl)-5-methyl-4-oxazolyl]methyl]thio]-N-(2-phenylethyl)acetamide), iCRT 14 (:5-[[2, 5-Dimethyl-1-(3-pyridinyl)-1H-pyrrol-3-yl]methylene]-3-phenyl-2,4-thiazolidinedion), ICG 001 ((6S,9aS)-Hexahydro-6-[(4-hydroxyphenyl)methyl]-8-(1-naphthalenylmethyl)-4,7-dioxo-N-(phenylmethyl)-2H-pyrazino[1,2-a]pyrimidine-1(6H)carboxamide), XAV-939 (2-(4-(trifluoromethyl)phenyl)-7,8-dihydro-5H-thiopyrano [4,3-d]pyrimidin-4-ol), KY02111 (Benzenepropanamide, N-(6-chloro-2-benzothiazolyl)-3,4-dimethoxy-), or physiologically-acceptable salts thereof. In certain embodiments, a combination or at least two of these compounds is administered.

Another aspect of the invention provides a method for treating the orthopedic disease including administering a composition including a therapeutically effective amount of an inhibitor of bone morphogenetic protein (BMP) signaling. The composition may be administered as described above, for example in-utero and/or after birth of the subject. The subject may be a subject having an elevated level of BMP signaling. In certain embodiments, the level of BMP signaling is determined and the treatment administered on the basis of this level.

In certain embodiments, the inhibitor of BMP signaling is dorsomorphin (6-[4-[2-(1-Piperidinyl)ethoxy]phenyl]-3-(4-pyridinyl)-pyrazolo[1,5-a]pyrimidine), K 02288 (3-[(6-Amino-5-(3,4,5-trimethoxyphenyl)-3-pyridinyl]phenol), DMH-1 (4-[6-[4-(1-Methylethoxy)phenyl]pyrazolo[1,5-a]pyrimidin-3-yl]-quinoline), LDN 193189 (4-(6-(4-(piperazin-1-yl)phenyl)pyrazolo[1,5-a]pyrimidin-3-yl)quinolone) or physiologically-acceptable salts thereof. For example, the inhibitor of BMP signaling is dorsomorphin dihydrochloride or LDN 193189 trihydrochloride. In certain embodiments, a combination or at least two of these compounds is administered. In other embodiments, a combination of at least one inhibitor of beta-catenin signaling and at least one inhibitor of BMP signaling is administered.

Pharmaceutical Compositions

Another aspect of the present invention provides pharmaceutical compositions including at least one inhibitor of beta-catenin signaling or at least one inhibitor of BMP signaling or a combination thereof.

The pharmaceutical compositions can be in the form of, for example, tablets, pills, dragees, hard and soft gel capsules, granules, pellets, aqueous, lipid, oily or other solutions, emulsions such as oil-in-water emulsions, liposomes, aqueous or oily suspensions, syrups, alixiers, solid emulsions, solid dispersions or dispersible powders. In pharmaceutical compositions for oral administration, the agent may be admixed with commonly known and used adjuvants and excipients, for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GELUCIRE). In the pharmaceutical composition, the agent may also be dispersed in a microparticle, e.g. a nanoparticulate, composition.

For parenteral administration, the agent or pharmaceutical compositions of the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally, for parenteral administration the agent or pharmaceutical compositions of the agent can be in the form of an aqueous, lipid, oily or other kind of solution or suspension or even administered in the form of liposomes or nano-suspensions.

Mode of Administration

The pharmaceutical compositions may be administered by any method that allows for the delivery of a therapeutic effective amount of the agent to the subject. Modes of administration can include, but are not limited to oral, topical, transdermal and parenteral routes, as well as direct injection into a tissue and delivery by a catheter. Parenteral routes can include, but are not limited to subcutaneous, intradermal, intra-articular, intravenous, intraperitoneal and intramuscular routes. In one embodiment, the route of administration is by topical or transdermal administration, such as by a lotion, cream, a patch, an injection, an implanted device, a draft or other controlled release carrier. Routes of administration include any route which directly delivers the composition to the systemic circulation (e.g., by injection), including any parenteral route.

When the composition is delivered in-utero, it may be delivered by for example, a parenteral route, for example, by intraperitoneal delivery.

One embodiment of the method of the invention includes administering the composition in a dose, concentration and for a time sufficient to prevent the development of, or to lessen the extent of the genetic bone disease. Certain embodiments include administering systemically the composition in a dose between about 0.1 micrograms and about 100 milligrams per kilogram body weight of the subject, between about 0.1 micrograms and about 10 milligrams per kilogram body weight of the subject, between about 0.1 micrograms and about 1 milligram per kilogram body weight of the subject. In practicing this method, the composition can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound.

Methods for Identifying Compounds for Treating a Genetic Orthopedics Disease

Another aspect of the invention provides methods for identifying compounds for treating a genetic orthopedic disease. In one embodiment, the method includes administering a test compound to an $Axin1^{Prx1}$ non-human mammalian embryo and examining an elbow joint of the embryo to determine the extent of separation of the humerus, radius and ulna. In one embodiment, the non-human mammalian embryo is a mouse embryo.

Compounds that exhibit at least a predetermined separation of the humerus, radius and ulna are identified as compounds for treating the genetic orthopedic disease. In one embodiment, the examination is by x-ray analysis. In some embodiments, the method includes comparing the extent of separation of the humerus, radius and ulna to that observed in a $Axin1^{Prx1}$ non-human mammalian embryo, for example a $Axin1^{Prx1}$ mouse embryo, that has not been exposed to the test compound.

Embodiments of the invention will be further described in the following examples, which do not limit the scope of the invention described in the claims.

Example 1—Generation of a Conditional Allele of Mouse Axin1

To circumvent the early lethality (E9.5) observed in Axin1 global knockout (KO) mice (Zeng et al., 1997) and to assess the specific role of Axin1 in skeletal development and postnatal bone homeostasis, we generated a strain of mice that carry targeted alleles of Axin1 ($Axin1^{flox/flox}$ mice) allowing for conditional deletion of the Axin1 gene when bred with mice expressing Cre recombinase (Xie et al., 2011).

The function of Axin1 in vivo is poorly understood because Axin1 KO mice are embryonic lethal at E9.5 or E10.5 (Zeng et al., 1997). We generated a conditional targeted allele of Axin1, the $Axin1^{flox/flox}$, mice. The short (2.6-kb) and long (7.4-kb) homologous arms for the targeting vector were isolated from a 129/sv mouse BAC library (RPCI-22 422B5). Since the exon2 of the Axin1 gene has been demonstrated to be essential for the function of Axin1 (Zeng et al., 1997), exon2 was flanked by two loxP sites in the targeting construct. A neomycin (neo) cDNA cassette, under the control of thymidine kinase (tk) promoter and flanked by two FRT sites was introduced at the 3'-end of the second loxP site. The diphtheria toxin A-fragment (DTA) driven by the phosphoglycerate kinase (PGK) promoter was also inserted at the 5'- and 3'-end of the vector, respectively (Xie et al., 2011). The linearized targeting construct was then introduced into ES cells by electroporation. ES clones resistant to G418 were screened for homologous recombination by Southern blotting. Two positive clones were injected into C57BL/6J blastocysts at the transgenic facility of the University of Texas (Houston, Tex.). Three chimeric mice were obtained, and one of these transmitted the targeted Axin1 locus to subsequent generations. The mice were genotyped by Southern blotting by 5' probe and by PCR using DNAs extracted from tail tissues (Xie et al., 2011). The neomycin cassette was deleted by crossing the resulting mice to the Rosa26-FLP mice (Farley et al., 2000; Xie et al., 2011). The Axin1$^{flox/flox}$ mice were viable and fertile, and did not present any recognizable phenotype.

The Axin1$^{-/-}$ homozygous embryos died at E9.5 or E10.5, displaying a wide spectrum of abnormalities including incomplete closure or malformation of head folds, crooked neural tube, cardia bifida and duplication of embryonic axis (Perry et al., 1995; Zeng et al., 1997). The Axin1$^{del/del}$ mice (CMV-Cre; Axin1$^{flox/flox}$) exhibit recessive embryonic defects similar to those caused by the null allele of Axin1$^{Tg1}$ (Perry et al., 1995; Zeng et al., 1997; Chia et al., 2009). Twenty-seven embryos from intercrossed Axin1$^{del/+}$ mice were examined at E10.5 and seven Axin1$^{del/del}$ homozygotes were found, consistent with the expected Mendelian ratio. Eighteen embryos from intercrossed Axin1$^{del/+}$ mice were also examined at E9.5. Four Axin1$^{del/del}$ homozygotes were found as the expected frequency. Next we performed Western blot analysis using cell lysates extracted from whole embryos (Xie et al., 2011). Strong Axin1 band was observed in the Axin1$^{del/+}$ cells but no signal was visible for Axin1$^{del/del}$ cells. All embryos of the homozygotes were severely abnormal. They were significantly smaller than their wild-type or heterozygous littermates and displayed underdeveloped head folds and open head folds (Xie et al., 2011). The embryos of heterozygotes were indistinguishable from that of wild-type littermates (data not shown). Therefore, the deleted allele should represent a null allele of Axin1.

Example 2—Specific Deletion of Axin1 in Limb Mesenchymal Stem Cells (MSCs) Leads to Fibular Hemimelia (FH), Tarsal Coalition (TC) and Humeroradial Synostosis (HRS) Phenotypes Inactivation of Axin1 in limb MSCs results in defects in fibula development. In order to determine the role of Axin1 in skeletogenesis, we generated Axin1$^{Prx1}$ mice by breeding the Axin1$^{flox/flox}$ mice with Prx1-Cre transgenic mice (Logan et al., 2002) in which the Cre expression is under the control of the Prx1 promoter. This Prx1 (paired-related homeobox gene-1) regulatory element leads to Cre expression throughout the early limb bud mesenchyme and in a subset of craniofacial mesenchyme. Crossing Prx1-Cre mice to a reporter mouse harboring a floxed Cre-reporter cassette revealed that recombinase activity is first observed in the earliest limb bud at E9.5. By early to mid-bud stages at E10.5 recombination is essentially complete in all mesenchymal cells in the limb (Logan et al., 2002). Prx1-Cre mice were generated in Dr. Cliff Tabin's lab (Harvard University) and were deposited in Jackson Lab. We obtained this mouse strain from Jackson Lab (Bar Harbor, Me., C57BL/6 background).

Figure 2B:
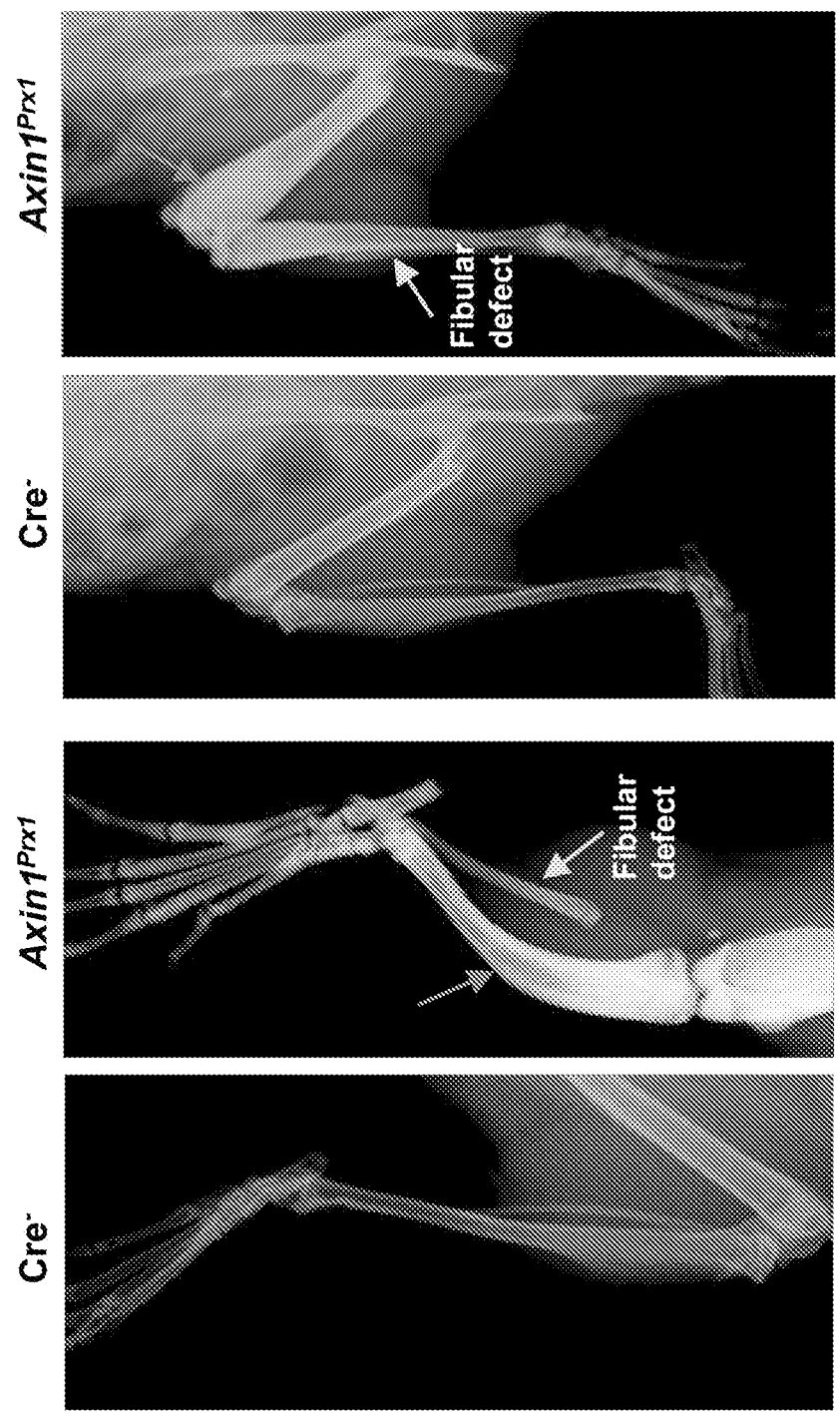
FIG. 2(b) shows defects in fibular development and increased bone density were observed Axin1$^{Prx1}$ KO Defect mice. X-ray radiographic analysis showed that partial developed but mineralized fibulae (mild fibular hypoplasia) were observed in two of 8-week-old Axin1$^{Prx1}$ KO mice (<30% loss, 2/52) (2nd left and far right) (upper arrows). In addition, bone mineral density was also increased in Axin1$^{Prx1}$ KO mice (lower arrows).
Figure 2C:
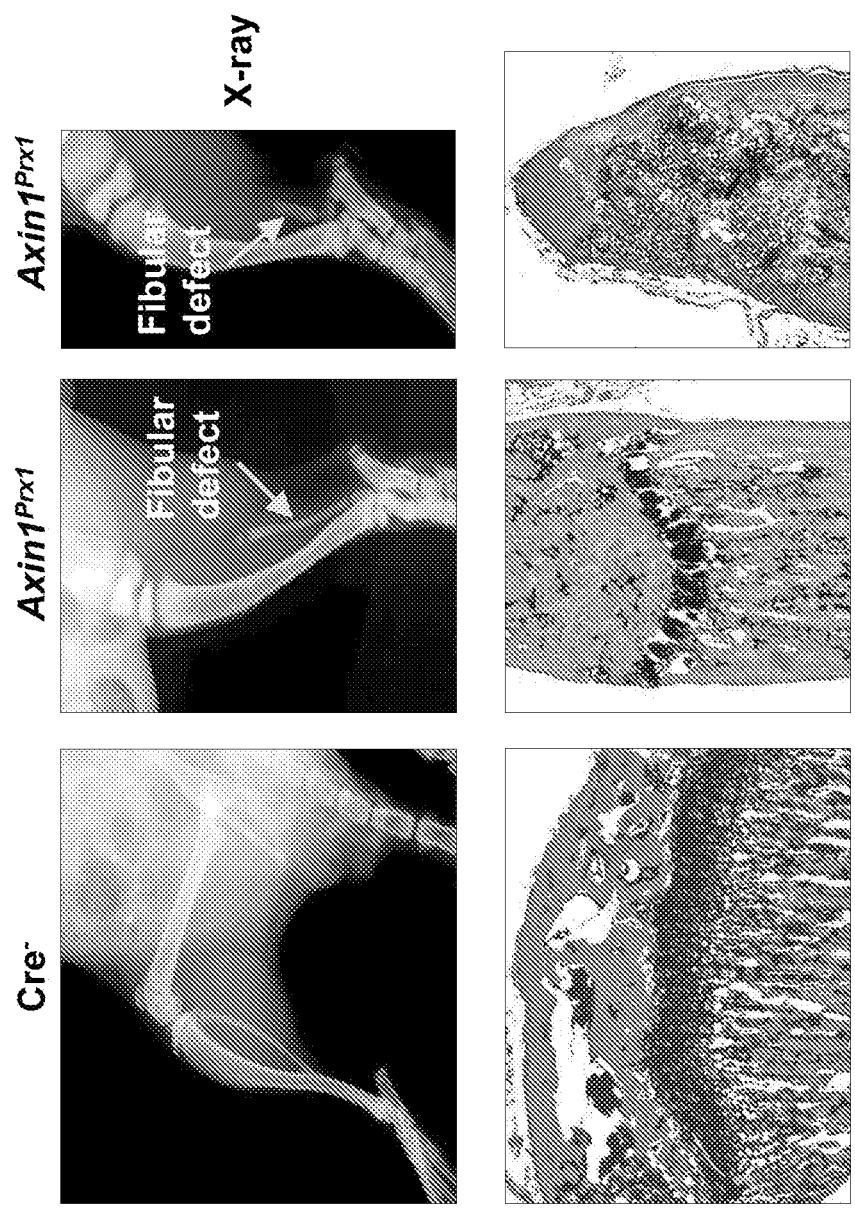
FIG. 2(c) shows defects in fibular development in Axin1$^{Prx1}$ KO mice. Fibular tissues were dissected from 8-week-old Cre-negative and Axin1$^{Prx1}$ KO mice. Histological analysis (Alcian blue/H&E staining, lower panel) showed that disorganized fibular structure, abnormal cartilage development and significant increase in bone mass was observed in Axin1$^{Prx1}$ KO mice.

We first examined skeletal development at E13.5, E16.5 and postnatal day 7 stages by Alizarin red/Alcian blue staining. The one not notable defect is the presence of various fibular deficiencies in the Axin1$^{Prx1}$ homozygous embryos and postnatal mice (FIG. 1). Radiographic analysis of 1- and 2-week-old mice showed that the absence of the fibula in some of Axin1$^{Prx1}$ mice was complete or almost complete (>50%, 27/52) where only a distal, vestigial fragment was present (FIG. 2A). The other Axin1$^{Prx1}$ mice had partial absence of the fibula (30-50%, 23/52) in which the proximal portion of the fibula was absent while the distal portion was present but could not support the ankle (FIG. 2A). And the mild fibular hypoplasia was observed in some Axin1$^{Prx1}$ mice (2/52), in which the fibula was absent less than 30% of its length (FIG. 2B, $2^{nd}$ left and far right). These results indicate that Axin1 plays an essential role in fibular development. In addition to the fibular absence or hypoplasia, we also observed several additional skeletal defects in Axin1$^{Prx1}$ mice. All femora of Axin1$^{Prx1}$ mice were shorter and wider than those of their Cre-negative littermates (FIG. 2B, far right). The bowed tibia was observed (FIG. 2B, $2^{nd}$ left). The valgus ankle was also seen and the tarsal coalitions were also found in the Axin1$^{Prx1}$ mice. Histological analysis showed that partially developed fibular tissues dissected from Axin1$^{Prx1}$ mice had high bone mass and poorly developed growth plate (FIG. 2C). The number of chondrocytes was significantly reduced and the structure of growth plate chondrocytes was disorganized (FIG. 2C). It is interesting to note that these skeletal defects observed in Axin1$^{Prx1}$ mice have been suggested to be the key features of FH disease in humans (Thompson et al., 1957; Achterman and Kalamchi, 1979; Stanitski and Stanitski, 2003). In summary, our preliminary data suggest that Axin1 is required for fibular development.

Figure 3:
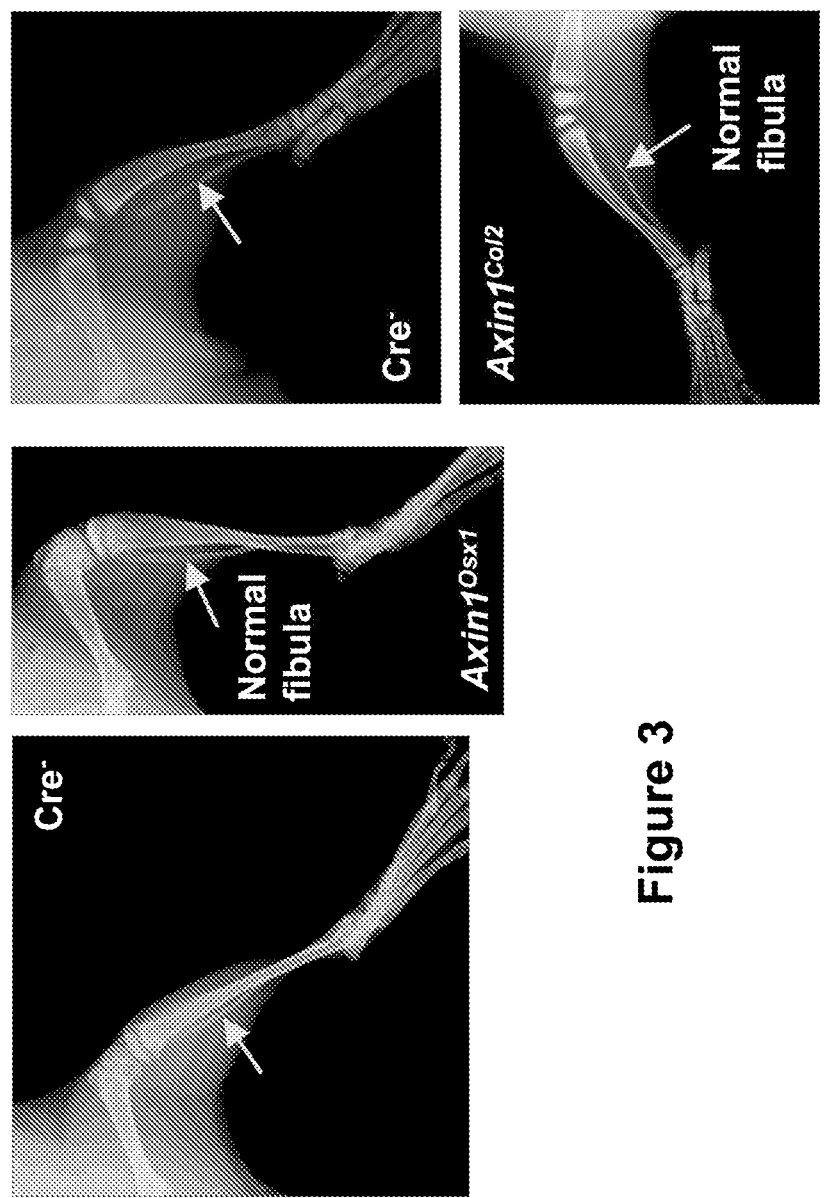
FIG. 3 shows normal fibular development observed in Axin1$^{Osx}$ and Axin1$^{Col2}$ KO mice. To determine if deletion of Axin1 in osteoblast precursor cells or in chondrocytes will exhibit similar defects in fibular development, we generated Axin1$^{Osx1}$ and Axin1$^{Col2}$ conditional KO mice. Radiographic analysis showed that fibular development was normal in both Axin1$^{Osx1}$ and Axin1$^{Col2}$ KO mice (4-week-old).

To determine the role of Axin1 in other cell populations, we bred Axin1$^{flox/flox}$ mice with Osx1-Cre (Rodda and McMahon, 2006) or Col2-Cre (Ovchinnikov et al., 2000) transgenic mice and generated Axin1$^{Osx1}$ and Axin1$^{Col2}$ conditional KO mice. We didn't observe fibular defects in Axin1$^{Osx1}$ (targeting deletion of Axin1 in Osx1-expressing osteoblast precursor cells) or Axin1$^{Col2}$ mice (targeting deletion of Axin1 in Col2-expressing chondrocytes) (FIG. 3). These results suggest that Axin1 plays a specific role in controlling fibular development within the MSC population.

Figure 4:
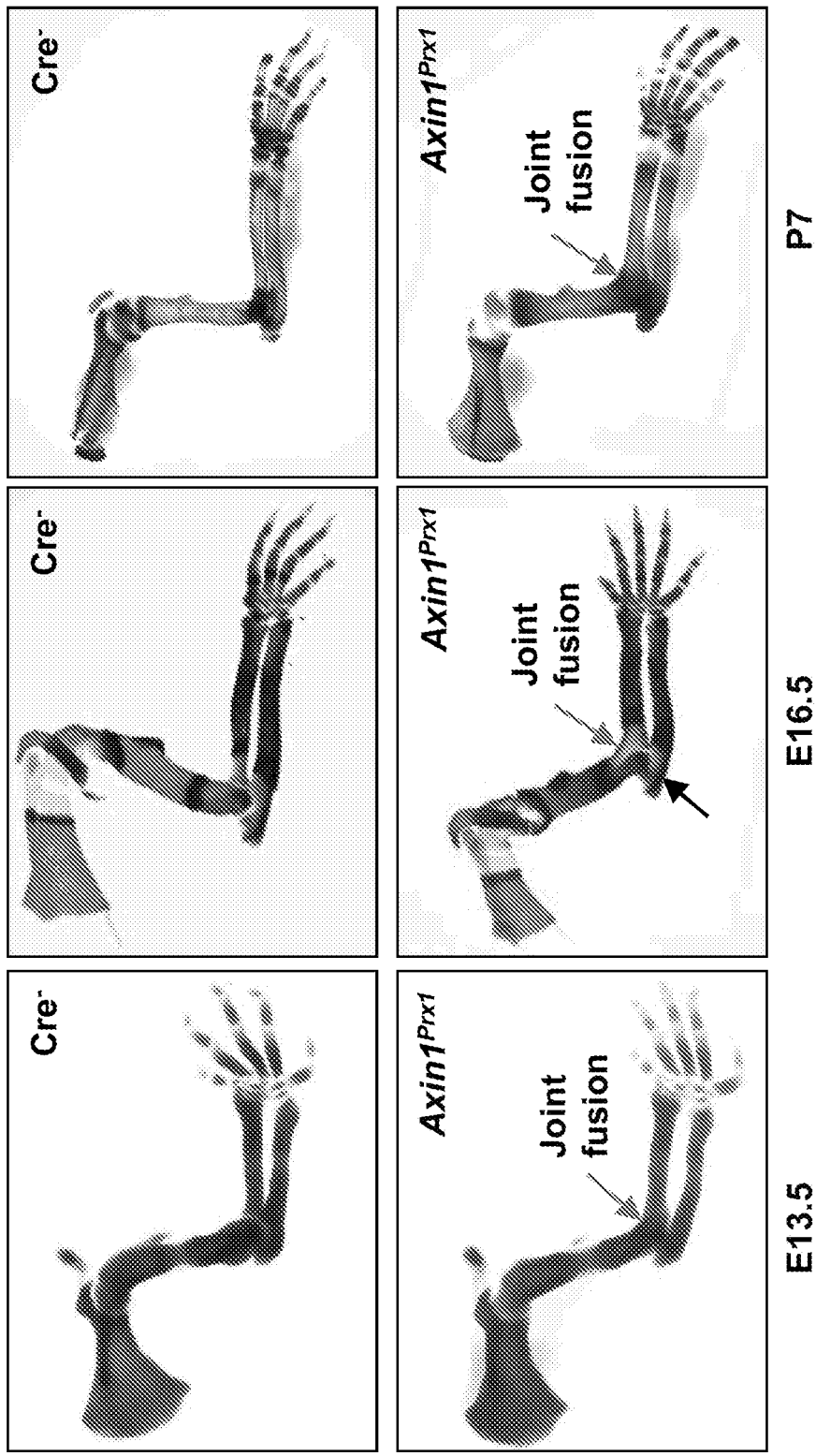
FIG. 4 shows the fusion of elbow joint observed in Axin1$^{Prx1}$ KO embryos and postnatal mice. Alizerin red/Alcian blue staining was performed in forelimbs of E13.5 and E16.5 embryos and postnatal day 7 mice. Red (upper) arrows indicate fusion of humerus and radius at E13.5, E16.5 and P7 Axin1$^{Prx1}$ KO embryos and mice. Black (lower) arrow indicates lateral fusion of humerus and ulna at E16.5 Axin1$^{Prx1}$ KO embryos.
Figure 5:
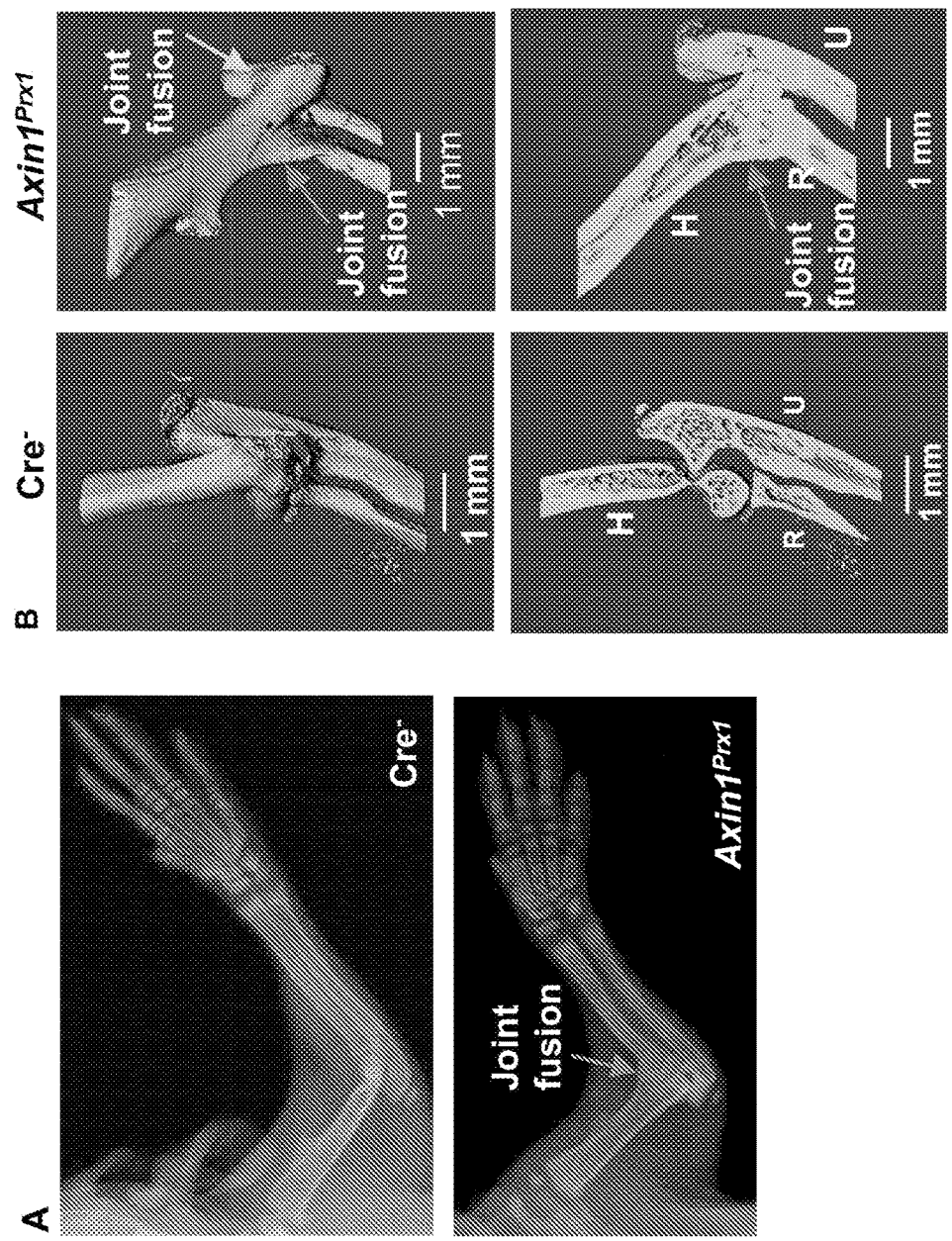
FIG. 5(A) shows that Axin1$^{Prx1}$ KO mice have joint fusion defects in forelimb. X-ray radiographic analysis (P12 mice) showed humeroradial and humerolunar fusions in Axin1$^{Prx1}$ KO mice (red arrows, A: lower panel).
FIG. 5(B) μCT analysis (P30 mice of three dimensional volumetric reconstructions of elbow joint and medial cross sections through the reconstructed volumes were generated. Red (left) arrows indicate fusion of humerus (H) and radius (R). Green (right) arrow indicates fusion of humerus (H) and ulna (U). It is worth noting that fusion between humerus and radius is a key characteristic of humeroradial synostosis in human.
Figure 6:
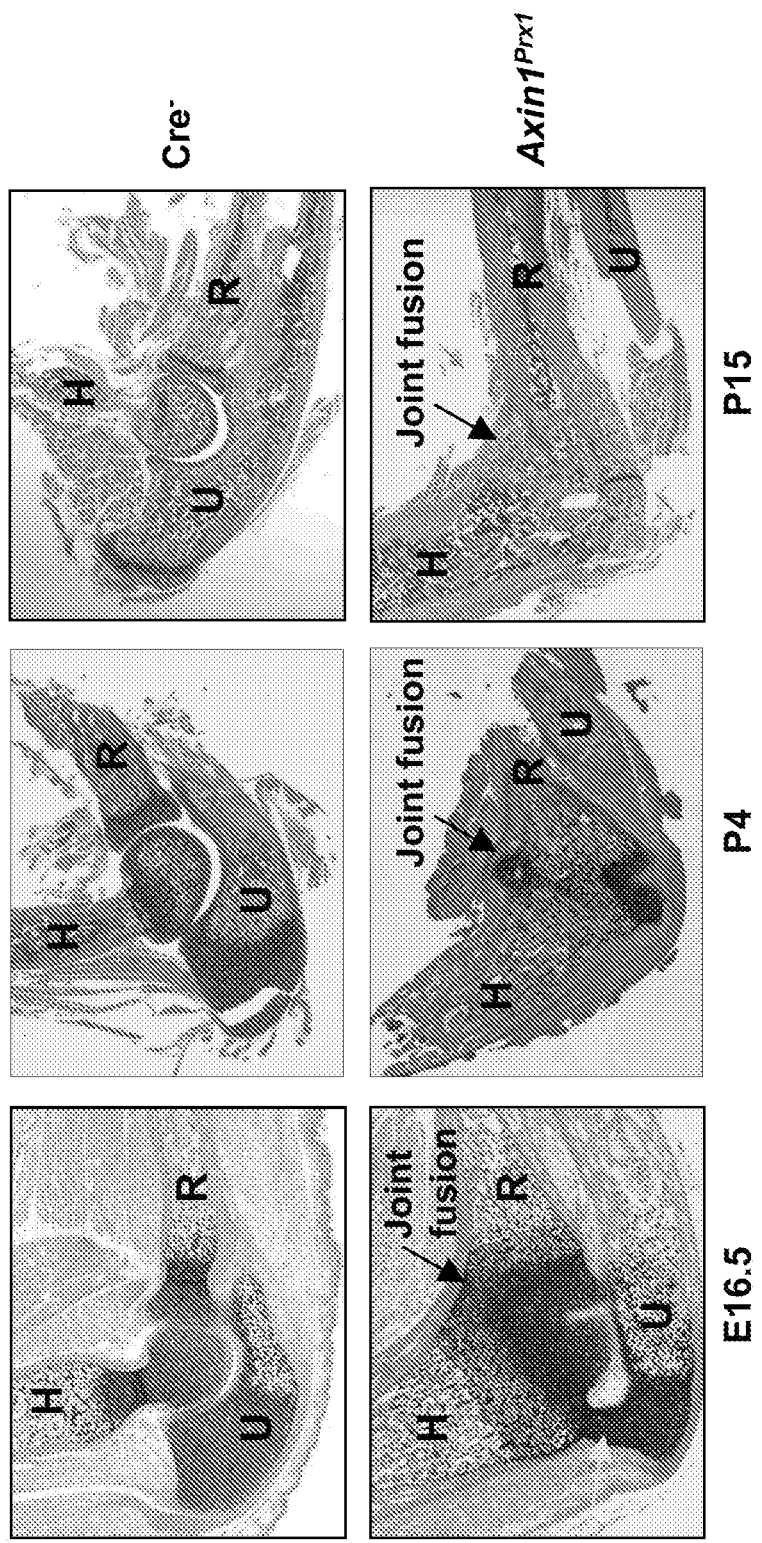
FIG. 6, Axin1$^{Prx1}$ KO mice have joint fusion defects in forelimb. Histological analysis of the elbow joint of Cre$^-$ and Axin1$^{Prx1}$ KO mice. Alcian Blue/Hematoxylin & Orange G stained sections of elbow of E16.5 embryos and and postnatal mice. The humerus H), radius and ulna are labeled. Axin1$^{Prx1}$ KO mice show fusion of humerus and radius (black (upper) arrows) and fusion of humerus and ulna (green (lower) arrow).
Figure 7:
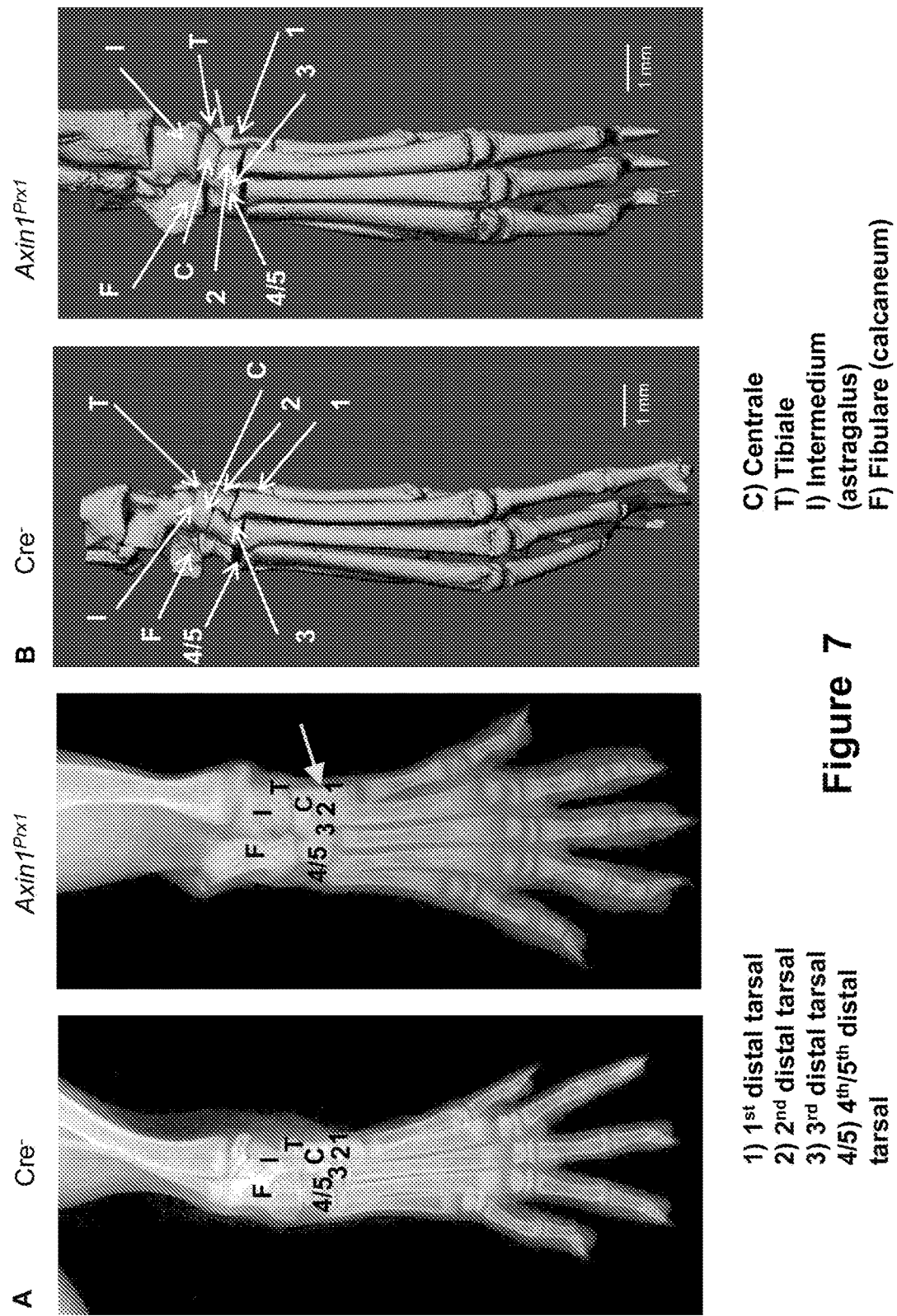
FIG. 7(A-B) shows fusion of tarsal elements observed in Axin1$^{Prx1}$ KO mice. Fusion of 1st, 2nd, 3rd, and 4th/5th tarsal elements and centrale in hind limb was observed by X-ray radiographic (A) and μCT analyses (B) in P15 Axin1$^{Prx1}$ KO mice (arrows). This is tarsal coalition (TC) like phenotype, (1) 1st distal tarsal, (2) 2nd distal tarsal, (3) 3rd distal tarsal, (4/5) 4th/5th distal tarsal, (C) Centrale, (T) Tibiale, (I) Intermedium (astragalus), (F) Fibulare (calcaneum)
Figure 8:
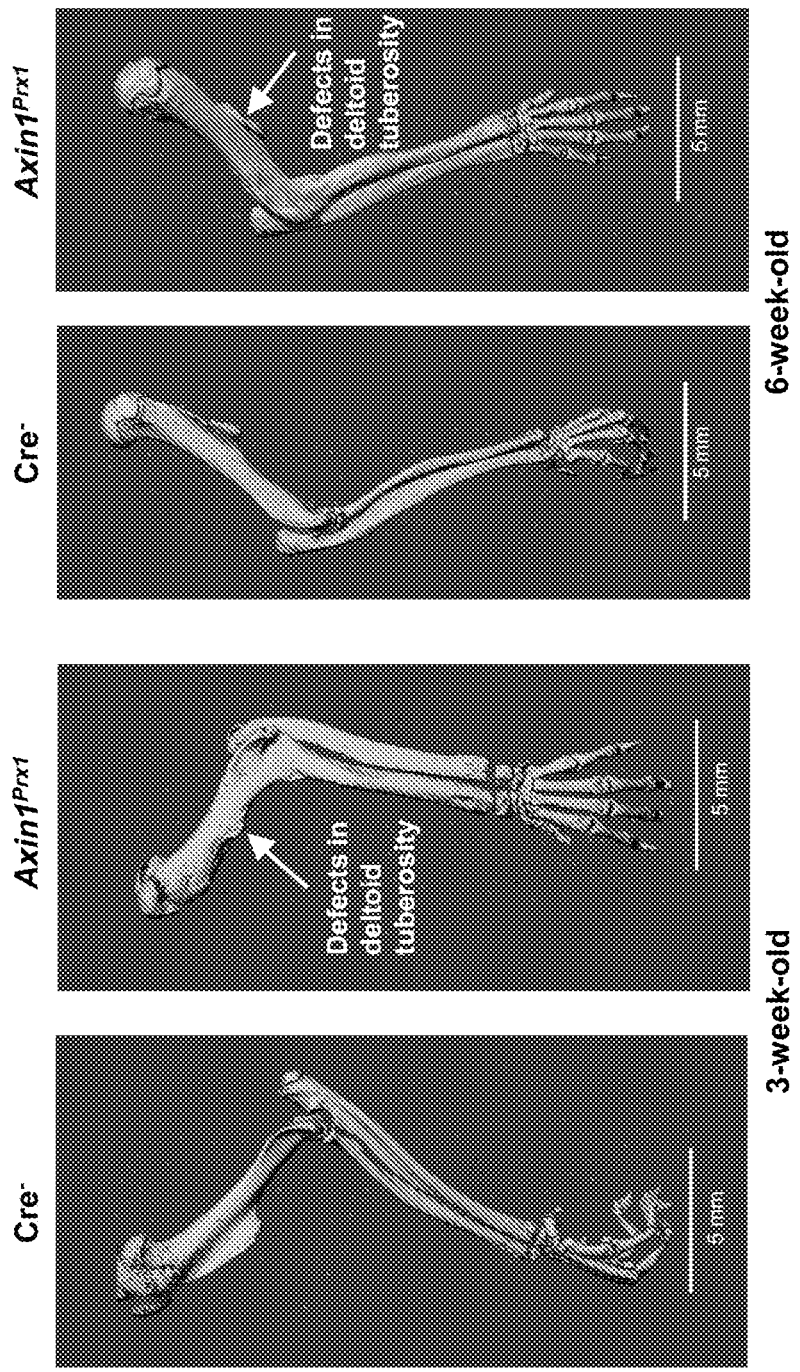
FIG. 8 shows Axin1$^{Prx1}$ KO mice having defects in deltoid tuberosity in forelimb. μCT analysis of forelimb of 3- and 6-week-old Cre- and Axin1$^{Prx1}$ mice. 3D images of forelimb were generated. The deltoid tuberosity in Axin1$^{Prx1}$ KO mice is much smaller than that of Cre-mice. Arrows indicate defects of deltoid tuberosity at the forelimb of Axin1$^{Prx1}$ KO mice.

Inactivation of Axin1 in limb MSCs resulted in synovial joint fusion in mice. Another notable defect observed in Axin1$^{Prx1}$ mice was that the synovial joints were fused. Specifically, the fusion of joint was apparent at elbow, where the humeroradial and humerolunar fusions were observed. Alizarin red/Alcian blue stained skeletal preparations of forelimbs showed that Axin1$^{Prx1}$ embryos exhibited single joint fusions of the humerus and radius, humerus and ulna in the forelimbs of E13.5 and E16.5 embryos and postnatal P7 mice, whereas control embryos showed a clear cavitation of joint and separation of the three skeletal elements (FIG. 4). Analysis by radiographs in P12 Axin1$^{Prx1}$ mice (FIG. 5A) and by μCT in P30 Axin1$^{Prx1}$ mice (FIG. 5B) revealed that the humeroradial and humerolunar fusions in the forelimbs of Axin1$^{Prx1}$ mice. Histologic examination of Axin1$^{Prx1}$ forelimb sections at P4 and P15 showed humeroradial fusions (FIG. 6). In addition, radiographic and μCT analyses revealed fusion of tarsal elements in Axin1$^{Prx1}$ mice. The $2^{nd}$ distal tarsal, $3^{rd}$ distal tarsal, $4^{th}$ & $5^{th}$ distal tarsal and centrale form a continuous skeletal element (FIG. 7). Analysis by μCT also exhibited defect of the deltoid tuberosity in 3- and 6-week-old Axin1$^{Prx1}$ mice (FIG. 8). Taken together, Axin1 is required for synovial joint formation.

Figure 9:
FIG. 9 shows Axin1$^{Prx1}$/Axin2$^{+/-}$ double mutant mice having more severe defects in skeletal development. Axin1$^{Prx1}$/Axin2$^{+/-}$ double mutant mice were generated. The size of 3-week-old Axin1$^{Prx1}$/Axin2$^{+/-}$ double mutant mouse is much smaller than that of (Axin1$^{flox/+}$)$^{Prx1}$/Axin2$^{+/-}$ mice (no skeletal phenotype compared to WT mice) and Axin1$^{Prx1}$ KO mice.

Example 3—Axin1$^{Prx1}$/Axin2$^{+/-}$ Double Mutant Mice Have Much Severe Defects in Fibular Hemimelia (FH), Proximal Femoral Focal Deficiency (PFFD), Tarsal Coalition (TC) and Humeroradial Synostosis (HRS) Phenotypes than Axin1$^{Prx1}$ Mice Axin2 is the homolog of Axin1 and is 44% identical to Axin1 in their amino acid sequences. It has been reported that Axin1 and Axin2 proteins are functionally equivalent (Chia and Costantini, 2005). Axin2 null mice (Axin2$^{-/-}$) appeared craniofacial defects (Yu et al., 2005) and our lab has previously demonstrated the high bone mass phenotype in adult Axin2$^{-/-}$ mice (Yan et al., 2009). Although Axin2 mutant mice have no apparent fibula and synovial joint phenotype, we hypothesized that deletion of Axin1 in combination with deletion of one allele of Axin2 gene might result in more severe consequences for fibular development and synovial joint formation. The body size of the 3 week old Axin1$^{Prx1}$/Axin2$^{+/-}$ double mutant mice is much smaller than Axin1$^{Prx1}$ mice (FIG. 9). To date, we have analyzed 52 Axin1$^{Prx1}$ mice and all of them have a fibular deficiency phenotype, indicating that Axin1 is required for fibular development. 27/52 had almost complete missing of fibula (>50% loss), 23/52 had partial fibular development (30-50% loss), and 2/52 had weak fibular defects (<30% loss). In contrast, all Axin1$^{Prx1}$/Axin2$^{+/-}$ double mutant mice (n=15) displayed a complete absence of the fibula (FIG. 10(a)). These results suggest that both Axin1 and Axin2 are essential for fibular morphogenesis and development.

Figure 10A:
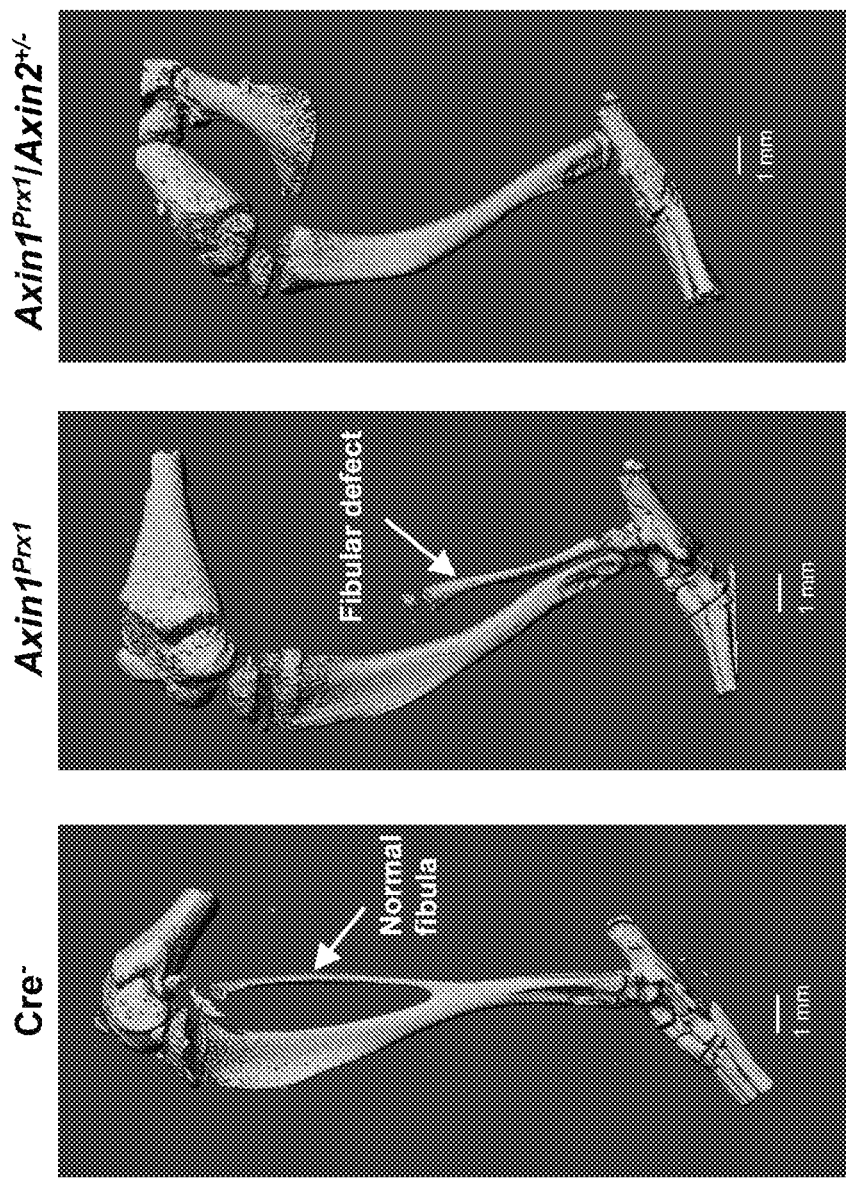
FIG. 10(a) shows Axin1$^{Prx1}$/Axin2$^{+/-}$ double mutant mice (3-week-old) having more severe defects in fibular development. 23 of Axin1$^{Prx1}$ KO mice (total 52 Axin1$^{Prx1}$ KO mice analyzed) had complete missing of fibula and 27 of Axin1$^{Prx1}$ KO mice (52 analyzed) had partial fibular development (middle panel). In contrast, all Axin1$^{Prx1}$/Axin2$^{+/-}$ double mutant mice (n=15) had complete missing of fibula (right panel). The Axin1$^{Prx1}$/Axin2$^{+/-}$ double KO mice have features resembling to proximal femoral focal deficiency (PFFD) phenotypes (right panel).
Figure 10B:
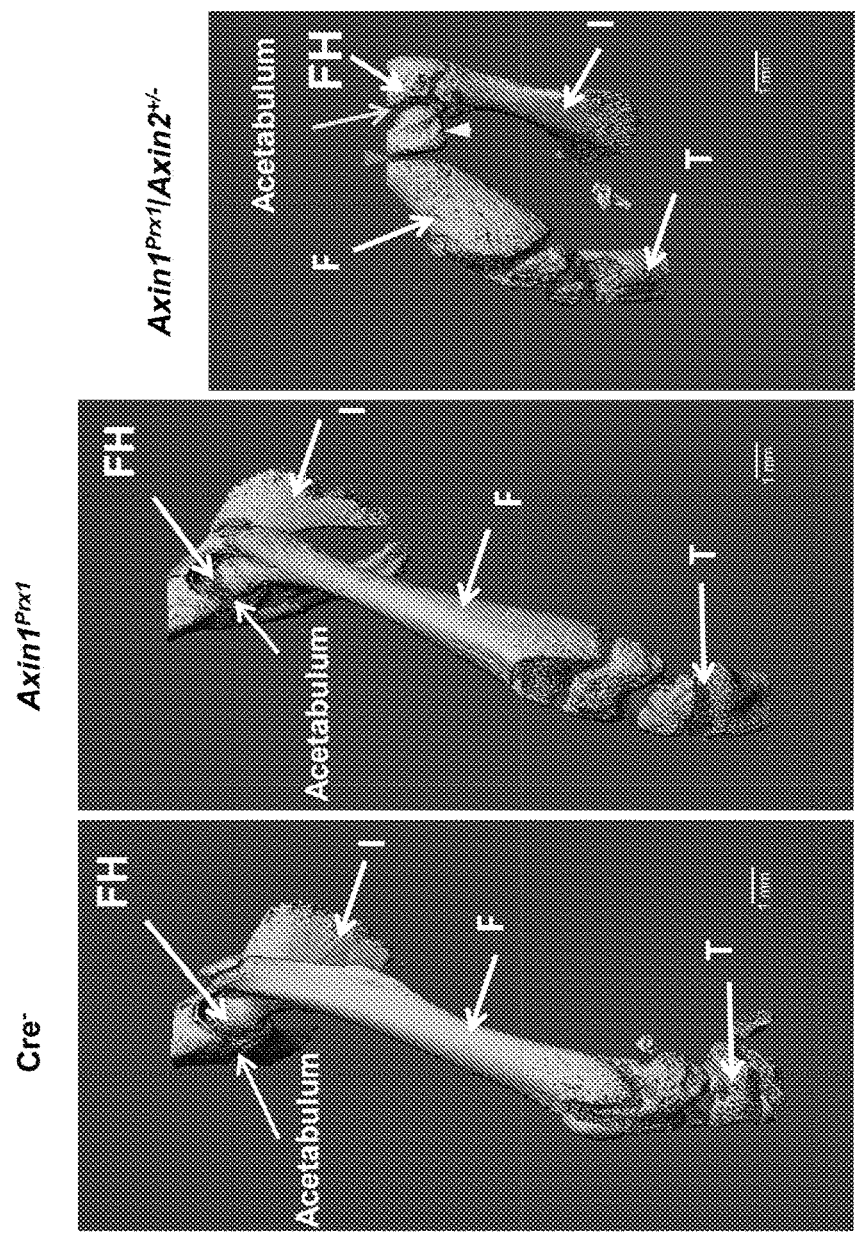
FIG. 10(b) shows Axin1$^{Prx1}$/Axin2$^{+/-}$ double KO mice having femoral defects phenotype resembling that of PFFD, which include: i) femoral length is reduced; ii) the femoral head is not fully developed; iii) no osseous connection between the femoral shaft and head; and iv) dysplasia of acetabulum.

In addition, the Axin1$^{Prx1}$/Axin2$^{+/-}$ double KO mice have features resembling to proximal femoral focal deficiency (PFFD) phenotypes (FIG. 10(a), right panel) Axin1$^{Prx1}$/Axin2$^{+/-}$ double KO mice have femoral defects phenotype resembling that of PFFD, which include: i) femoral length is reduced; ii) the femoral head is not fully developed; iii) no osseous connection between the femoral shaft and head; and iv) dysplasia of acetabulum (FIG. 10(a), 10(b)).

Figure 12:
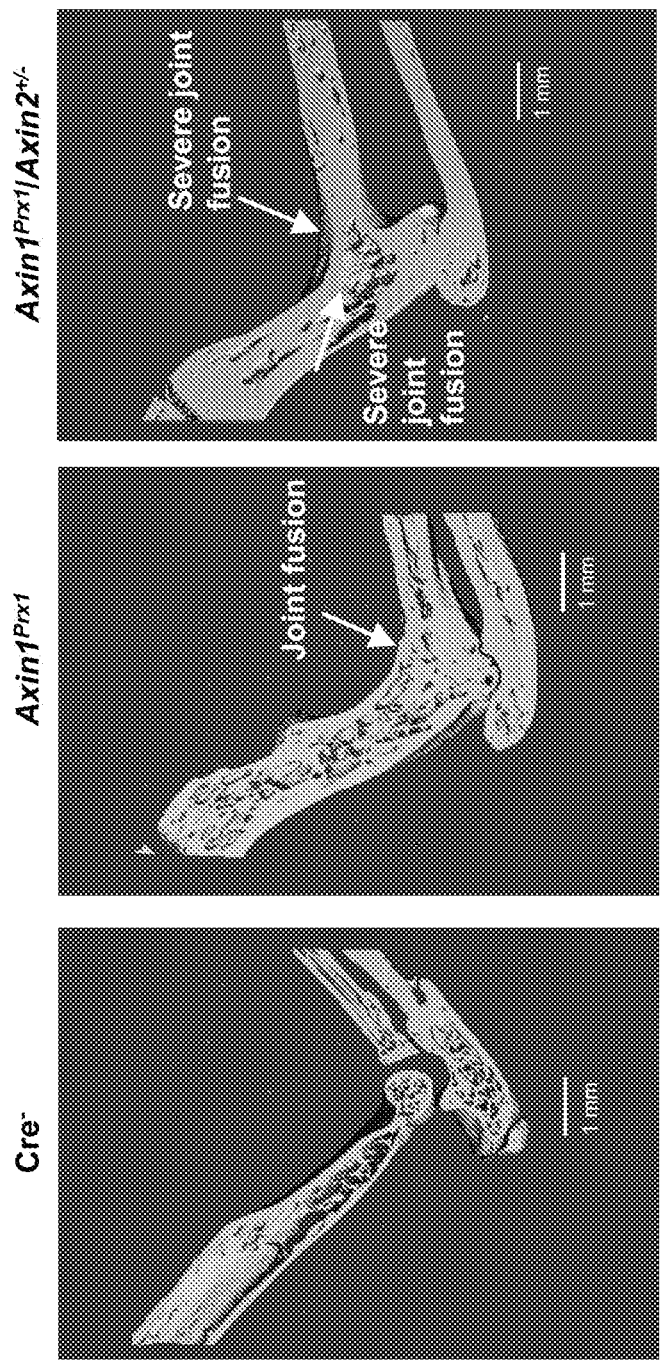
FIG. 12 shows Axin1$^{Prx1}$/Axin2$^{+/-}$ double KO mice having severe defects in joint fusion in forelimb. μCT analysis of elbow joints were performed in 3-week-old Cre$^-$, Axin1$^{Prx1}$ KO and Axin1$^{Prx1}$/Axin2$^{+/-}$ double KO mice. Medial cross sections of elbow joint through the reconstructed volumes were generated. More severe elbow joint fusion is observed in Axin1$^{Prx1}$/Axin2$^{+/-}$ double KO mice. The arrow in the central figure indicates the fusion of humerus and radius in Axin1$^{Prx1}$ KO mice. The upper arrow in the right figure indicates the severe fusion of humerus and radius in Axin1$^{Prx1}$/Axin2$^{+/-}$ double KO mice. The lower arrow in the right figure indicates the fusion of humerus and ulna in Axin1$^{Prx1}$/Axin2$^{+/-}$ double KO mice.
Figure 13:
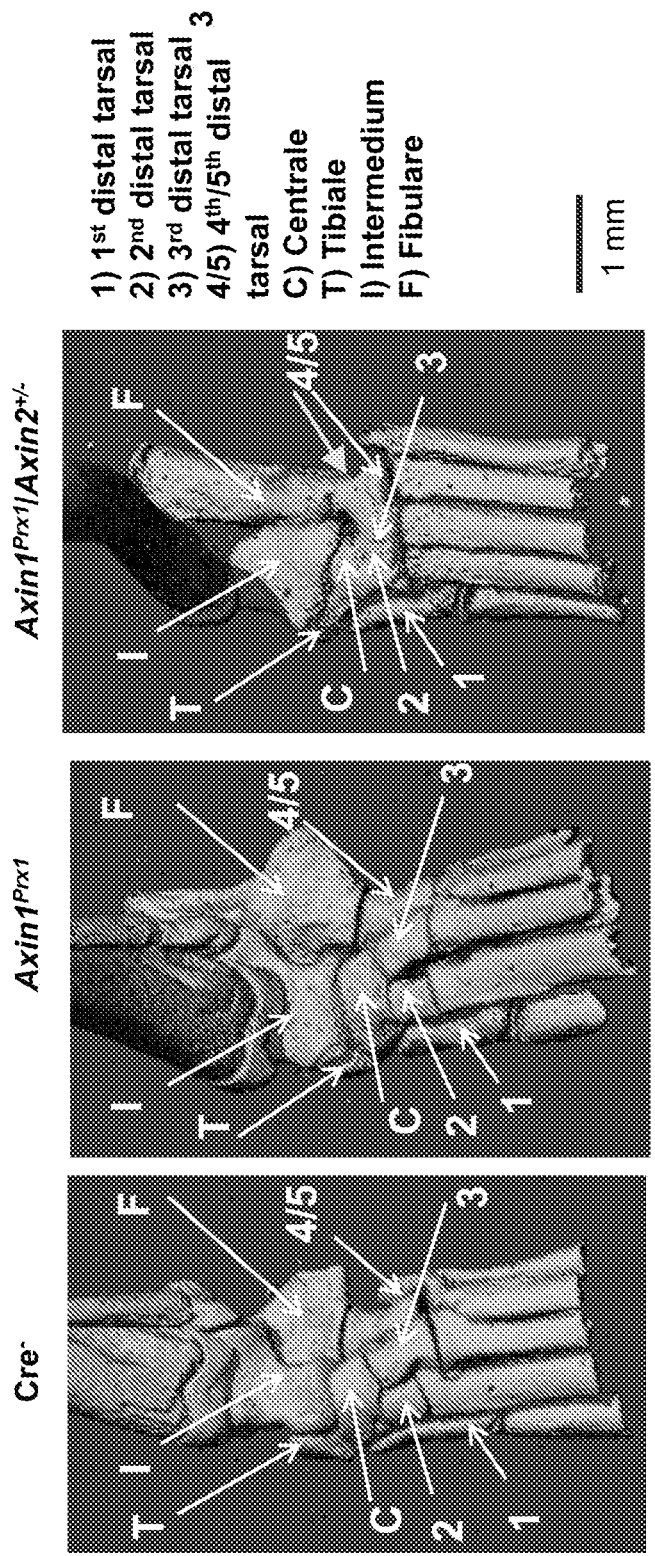
FIG. 13 shows Axin1$^{Prx1}$/Axin2$^{+/-}$ double KO mice having more severe tarsal coalition (TC) phenotypes. μCT analysis was performed in ankle joint of 3-week-old Cre$^-$, Axin1$^{Prx1}$ KO and Axin1$^{Prx1}$/Axin2+/– double KO mice. 3D images showed that most of the tarsal element of ankle joint, 2nd, 3rd, and 4th & 5th tarsal elements, centrale (C) Tibiale (T), Intermedium (I) (astragalus) and Fibulare (F) (calcaneum), are fused in Axin1$^{Prx1}$/Axin2$^{+/-}$ double KO mice (arrow).
Figure 14:
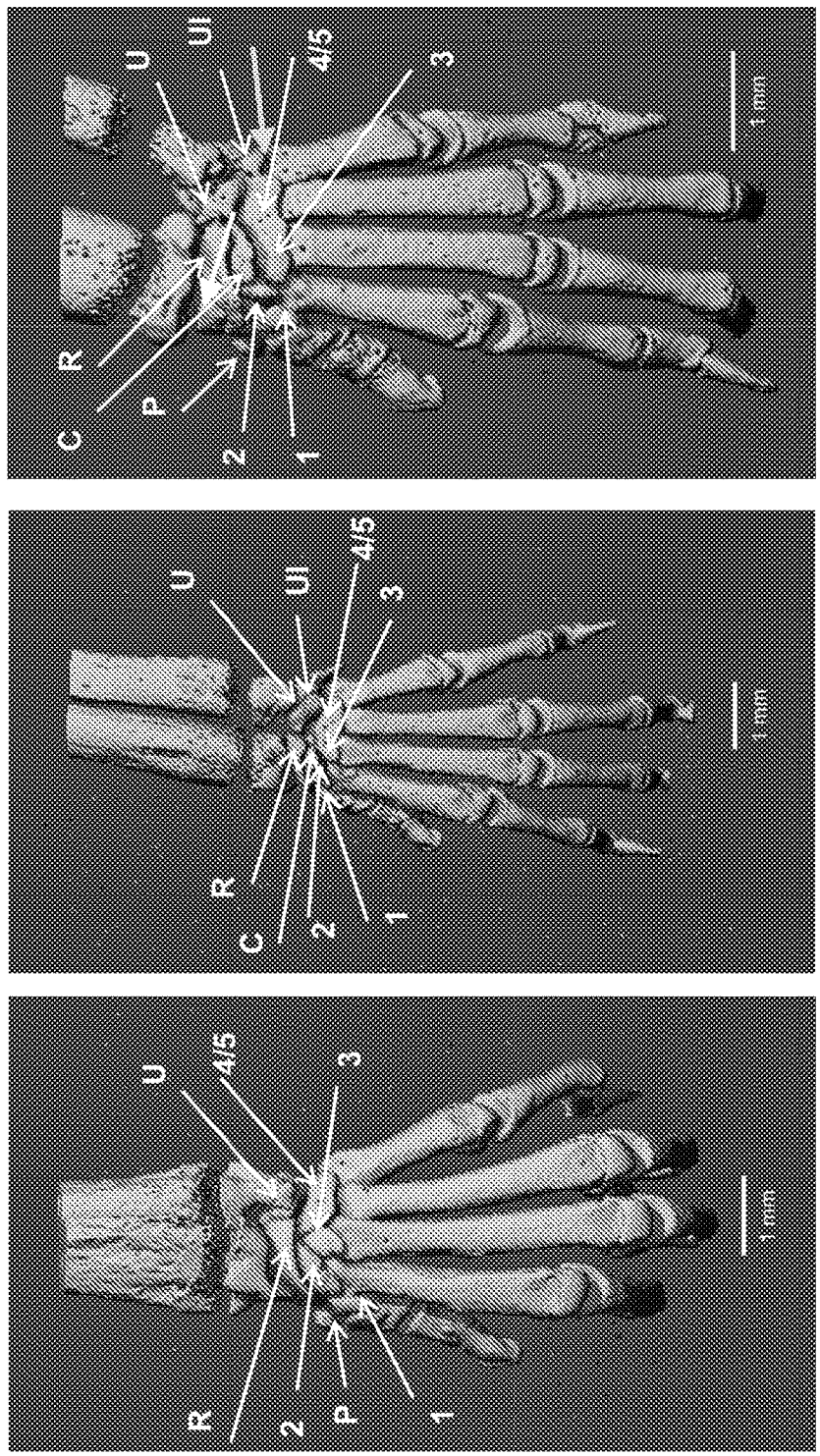
FIG. 14 shows Axin1$^{Prx1}$/Axin2$^{+/-}$ double KO mice having severe defects in fusion of carpal elements in forelimb. μCT analysis of wrist joint of 3-week-old Cre-, Axin1$^{Prx1}$ KO and Axin1$^{Prx1}$/Axin2$^{+/-}$ double KO mice showed that more severe wrist joint fusion was observed in Axin1$^{Prx1}$/Axin2$^{+/-}$ mice. The 3rd distal carpal, 4th/5th distal carpal, ulnare (U) and ulnar sesamoid (UI) formed a continuous element in the Axin1$^{Prx1}$/Axin2$^{+/-}$ double KO mice (arrow).
Figure 15:
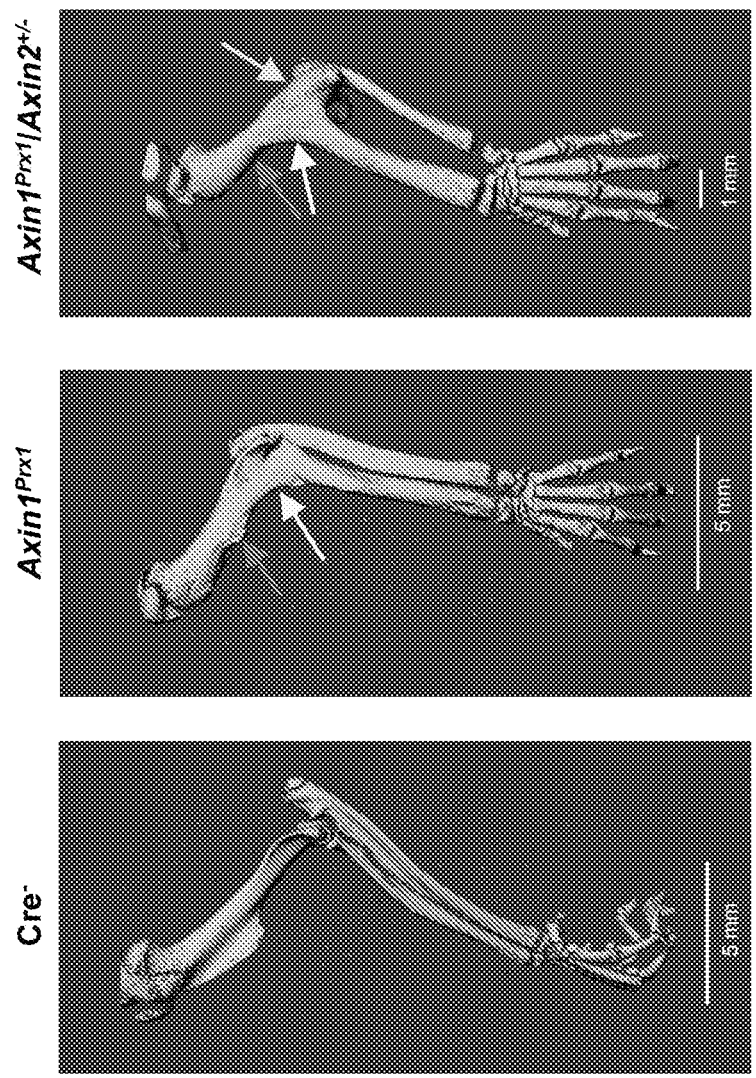
FIG. 15 shows Axin1$^{Prx1}$/Axin2$^{+/-}$ double KO mice having severe defects in joint fusion in forelimb. μCT analysis of forelimb of 3-week-old Cre$^-$, Axin1$^{Prx1}$ KO and Axin1$^{Prx1}$/Axin2$^{+/-}$ double KO mice showed that more severe elbow joint fusion was observed Axin1$^{Prx1}$/A in2$^{+/-}$ mice. Lower left arrows indicate the fusion of humerus and radius in Axin1$^{Prx1}$ KO mice and Axin1$^{Prx1}$/Axin2$^{+/-}$ double KO mice. The right arrow indicates the severe fusion of humerus and ulna in Axin1$^{Prx1}$/Axin2$^{+/-}$ double KO mice. The upper left arrows indicate that the deltoid tuberosity was almost completely missing in Axin1$^{Prx1}$ KO mouse and completely absent in Axin1$^{Prx1}$/Axin2$^{+/-}$ double KO mice.

As expected, the Axin1$^{Prx1}$/Axin2$^{+/-}$ mice showed more severe joint fusion in the elbow, wrist and ankle joint. Axin1$^{Prx1}$/Axin2$^{+/-}$ double mutant mice exhibit more severe humeroradial and humerolunar fusions (FIGS. 11 and 12). Analysis by radiographs and μCT revealed that almost all tarsal elements (2$^{nd}$ distal tarsal, 3$^{rd}$ distal tarsal, 4$^{th}$ & 5$^{th}$ distal tarsal, centrale, tibiale, intermedium and fibulare) were fused (FIG. 13) in 3-week-old Axin1$^{Prx1}$/Axin2$^{+/-}$ double mutant mice. The joint of wrist of the Axin1$^{Prx1}$/Axin2$^{+/-}$ mice also showed more severe phenotypes, the 3$^{rd}$ distal carpal, 4$^{th}$ & 5$^{th}$ distal carpal, ulnare and ulnar sesamoid formed a continuous element (FIG. 14). The deltoid tuberosity was totally absent in the Axin1$^{Prx1}$/Axin2$^{+/-}$ double mutant mice (FIG. 15). These data reveal that both Axin1 and Axin2 play essential roles in synovial joint development and indicate that endogenous Axin2 can partially compensate for the absence of Axin1 during joint formation.

Figure 16:
FIG. 16 shows that deletion of one allele of β-catenin significantly reversed joint fusion phenotype of Axin1$^{Prx1}$ KO mice. Xray radiographic analysis of forelimb of 12-week-old (Axin1$^{flox/+}$/β-catenin$^{flox/+}$)$^{Prx1}$ (a), Axin1$^{Prx1}$ (b) and (Axin1$^{flox/flox}$/β-catenin$^{flox/+}$)$^{Prx1}$ (c) mice showed that the elbow joint fusion was reversed in (Axin1$^{flox/flox}$/β-catenin$^{flox/+}$)$^{Prx1}$ mice (c). The arrow in (b) indicates that humerus and radius are fused in Axin1$^{Prx1}$ KO mice and the arrow in (c) indicates that the humerus and radius are clearly separated in Axin1$^{flox/flox}$/β-cat$^{flox/+}$)$^{Prx1}$ mice.
Figure 17:
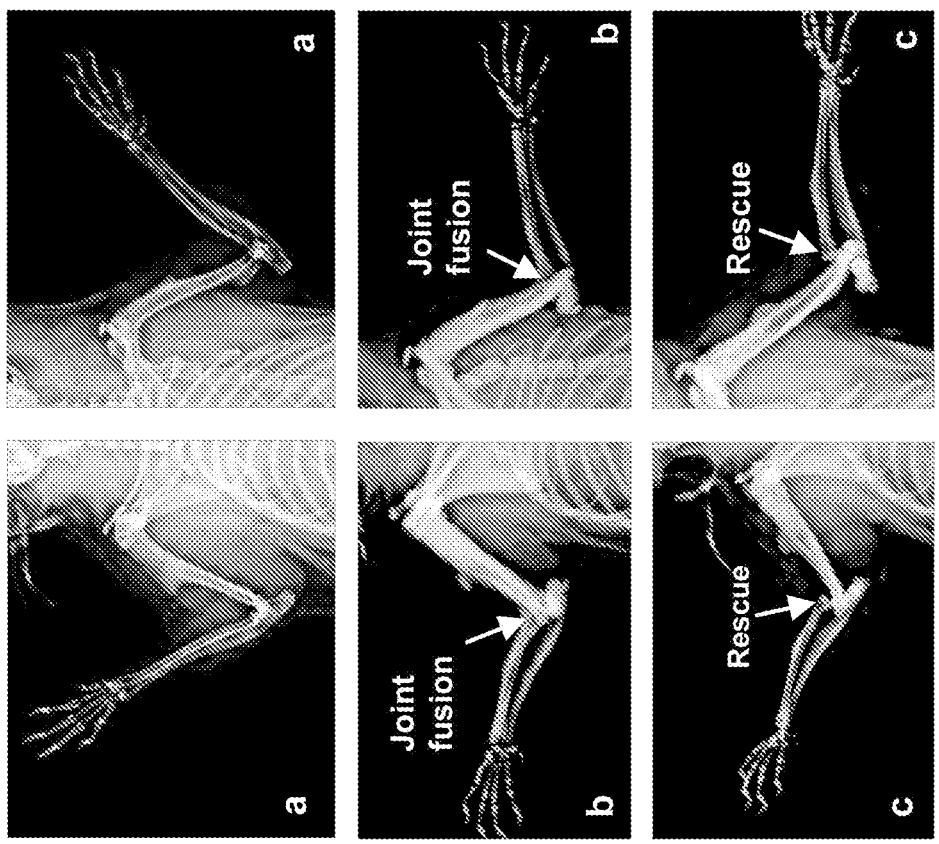
FIG. 17(A-C) shows that deletion of one allele of β-catenin significantly reversed joint fusion phenotype of Axin1$^{Prx1}$ KO mice. X-ray radiographic analysis of forelimb of 12-week-old (Axin1$^{flox/+}$/β-catenin$^{flox/+}$)$^{Prx1}$ (a), Axin1$^{Prx1}$ (b) and (Axin1$^{flox/flox}$/β-catenin$^{flox/+}$)$^{Prx1}$ (c) mice showed that the elbow joint fusion was reversed in (Axin1$^{flox/flox}$/β-catenin$^{flox/+}$)$^{Prx1}$ mice (c). Arrows in (b) indicate that the humerus and radius are fused in Axin1$^{Prx1}$ KO mice and arrows in (c) indicate the humerus and radius are clearly separated in (Axin1$^{flox/flox}$/β-catenin$^{flox/+}$)$^{Prx1}$ mice.
Figure 18:
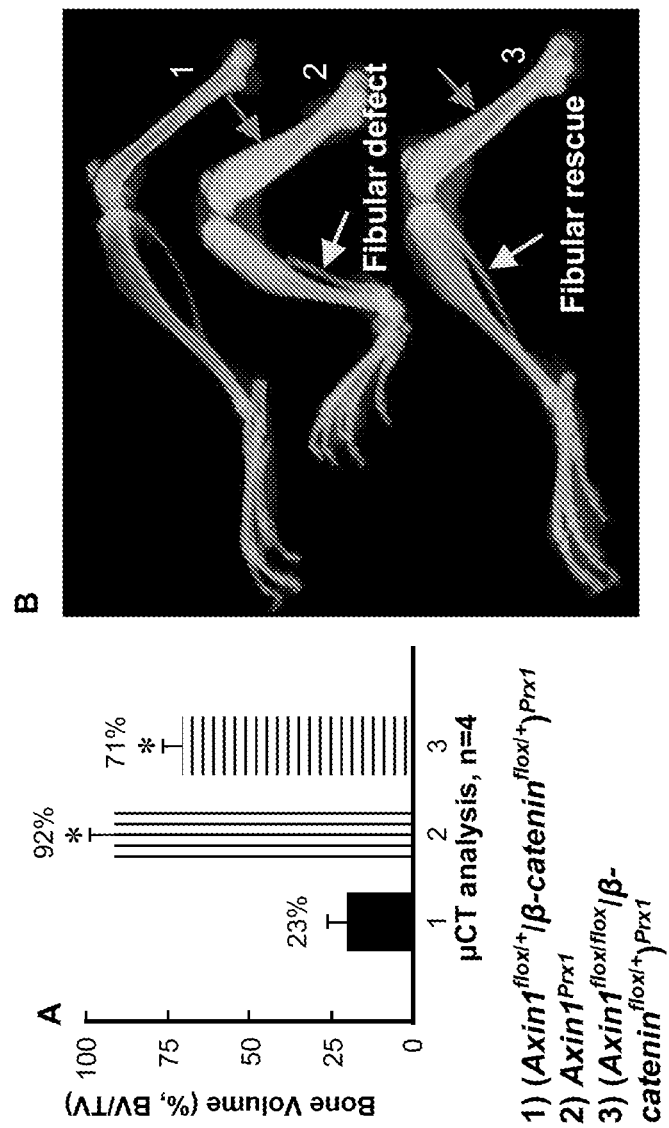
FIG. 18(A-B) shows that defects in fibular development of Axin1$^{Prx1}$ KO mice can be rescued by deletion of one allele of β-catenin. (A) X-ray radiographic analysis showed that defects in fibular development observed in 12-week-old Axin1$^{Prx1}$ mice (middle panel) were significantly reversed by deletion of one allele of β-catenin (lower panel). Dark arrows show bone mass increase. (B) μCT analysis showed that bone volume (BV) was increased to 92% in Axin1$^{Prx1}$ KO mice. Deletion of one allele of β-catenin caused BV reduction from 92 to 71%.
Figure 19:
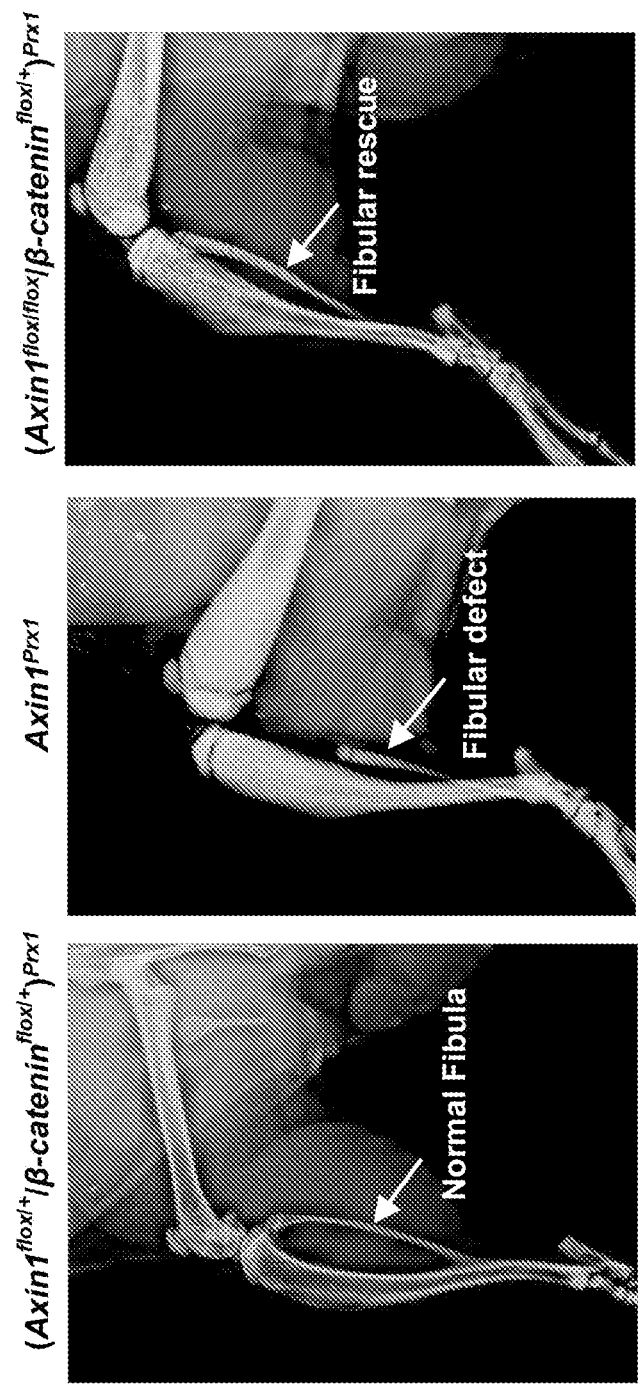
FIG. 19 Shows that deletion of one allele of β-catenin significantly reversed fibular defects observed in Axin1$^{Prx1}$ KO mice. Axin1$^{Prx1}$ KO mice were bred with β-catenin$^{flox/+}$ mice to produce (Axin1$^{flox/flox}$/β-catenin$^{flox/+}$)$^{Prx1}$ double mutant mice. Axin1$^{Prx1}$ mice (12-week-old) showed fibular defects (middle panel) and these were reversed by deletion of one allele of β-catenin (right panel).

Example 4—Deletion of One Allele of β-Catenin Significantly Reversed Fibular Hemimelia (FH) and Humeroradial Synostosis (HRS) Phenotypes in Axin1$^{Prx1}$ Mice Since Axin1 is a negative regulator of canonical Wnt signaling pathway, deletion of Axin1 will elevate β-catenin protein levels. If defects in skeletal development in Axin1$^{Prx1}$ mice are due to elevated levels of β-catenin, reducing the β-catenin (Ctnnb1) gene dosage might fully or partially correct defects observed in Axin1$^{Prx1}$ mice. On the other hand, if defects of skeletal development are β-catenin-independent, reducing the β-catenin gene dosage should have no effect. To test this hypothesis, we looked at genetic interaction between Axin1 and β-catenin in synovial joint formation. We found that defect in elbow joint in Axin1$^{Prx1}$ mice were alleviated in (Axin1$^{flox/flox}$/β-catenin$^{flox/+}$)$^{Prx1}$ mice (FIGS. 16 and 17). The radius and humerus are clearly separated in (Axin1$^{Prx1}$/β-catenin$^{flox/+}$)$^{Prx1}$ mice, although the joint is still dislocated (FIGS. 16 and 17). We found that deletion of one allele of the β-catenin gene in Axin1$^{Prx1}$ mice caused reduction of BV from 92 to 71% (FIG. 18A) and significantly reversed defects in fibular development (FIG. 18B). However, the rescuing is not complete and the fibula did not extend to the proximal end of tibia as observed in WT mice (FIG. 18B, FIG. 19). The bone density of the tibia is much higher and the shape of tibia is much wider in double mutant mice than Cre-negative mice (FIG. 18B, FIG. 19). These results demonstrate that Axin1 regulates the joint formation, fibular development and bone volume at least partially through the canonical Wnt/β-catenin pathway.

Figure 20:
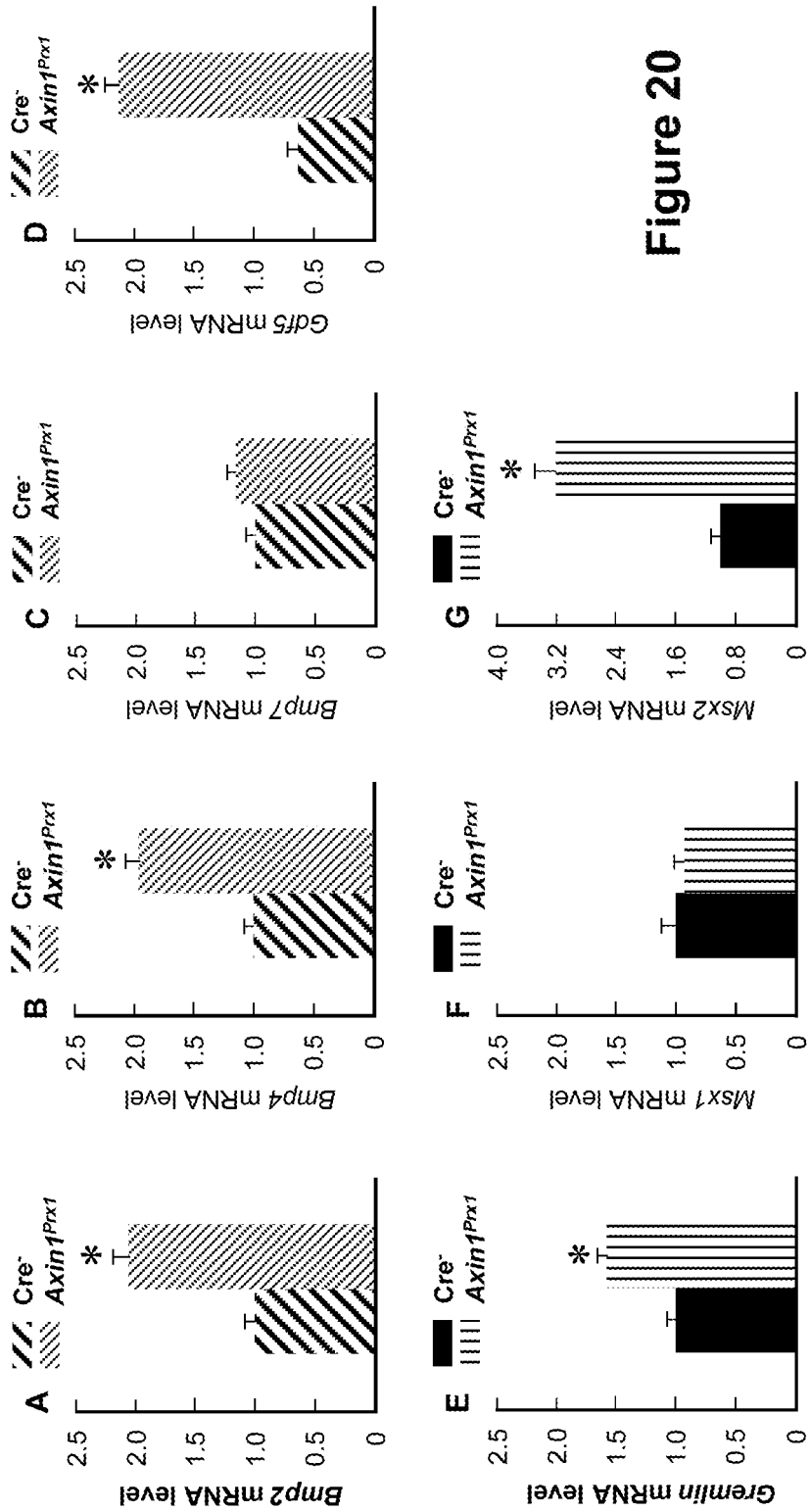
FIG. 20(A-G) shows that BMP signaling is up-regulated in Axin1$^{Prx1}$ conditional KO mice. Bmp2 (A), Bmp4 (A), Bmp7 (C), Gdf5 (D), Gremlin (E), Msx1 (F) and Msx2 (G). Total mRNA was extracted from E14.5 limbs of Cre-negative and Axin1$^{Prx1}$ KO embryos. Realtime PCR analysis showed that expression of Bmp2 (A), Bmp4 (B), Gdf5 (D), Gremlin (E), and Msx2 (G) was significantly up-regulated Axin1$^{Prx1}$ embryos.

Example 5—Inhibition of BMP Signaling Significantly Reversed FH and HRS Phenotypes Observed in Axin1$^{Prx1}$ Mice In previous studies, we found that Bmp2 and Bmp4 expression was up-regulated in Axin2 KO mice (Yen et al., 2009). To determine if BMP signaling is up-regulated in Axin1$^{Prx1}$ mice, we extracted total RNA from E14.5 hind limb of Cre-negative and Axin1$^{Prx1}$ embryos. We analyzed expression of several Bmp genes and BMP target genes and found that expression of Bmp2, Bmp4, Gdf5, Gremlin and Msx2 was significantly up-regulated in the limb tissues of Axin1$^{Prx1}$ embryos (FIG. 20).

Figure 21:
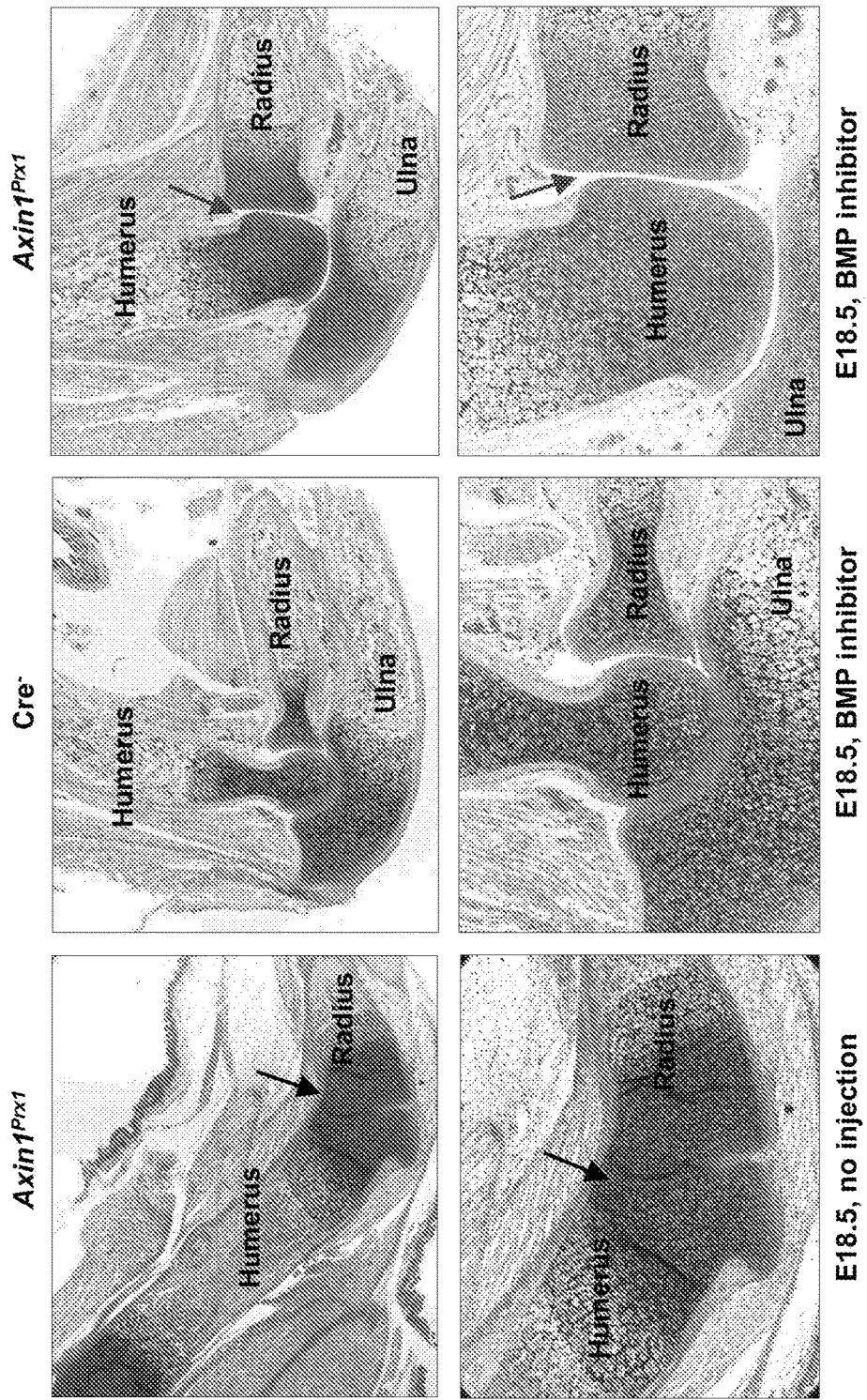
FIG. 21 show that inhibition of BMP signaling reversed joint fusion phenotype of Axin1$^{Prx1}$ KO mice. BMP inhibitor dorsomorphin (2.5 mg/kg, i.p. injection, single dose) was injected into pregnant mothers at E9.5 stage. Histological analysis showed that the humerus, radius and ulna are clearly separated in Axin1$^{Prx1}$ KO mice (right panel, arrow) which were treated with dorsomorphin. In contrast, histological sections of elbow joint of E18.5 Axin1$^{Prx1}$ KO mice without treatment of BMP inhibitor showed that the humerus and radius was fused in Axin1$^{Prx1}$ KO embryos (left panel, arrow). Lower panels: higher magnification.
Figure 22:
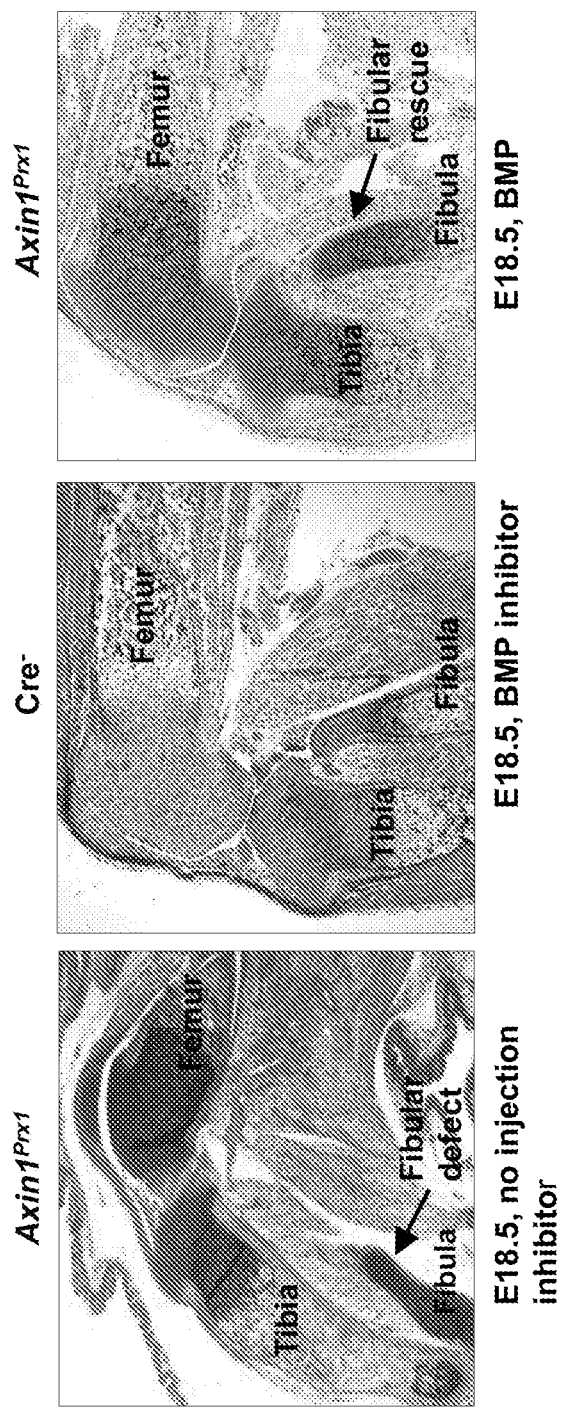
FIG. 22 shows that inhibition of BMP signaling reversed fibular defects observed in Axin1$^{Prx1}$ KO mice. BMP inhibitor dorsomorphin was given to pregnant mothers at E9.5 stage (Axin1$^{Prx1}$ mice were bred with Axin1$^{flox/flox}$ mice) (2.5 mg/kg, i.p. injection, single dose). Histology (Alcian Blue/Hematoxylin & Orange G staining) of hind limb of E18.5 Cre$^-$ and Axin1$^{Prx1}$ KO mice showed that administration of BMP inhibitor to Axin1$^{Prx1}$ KO mice significantly reversed fibular defects observed in Axin1$^{Prx1}$ KO mice (right panel).
Figure 24:
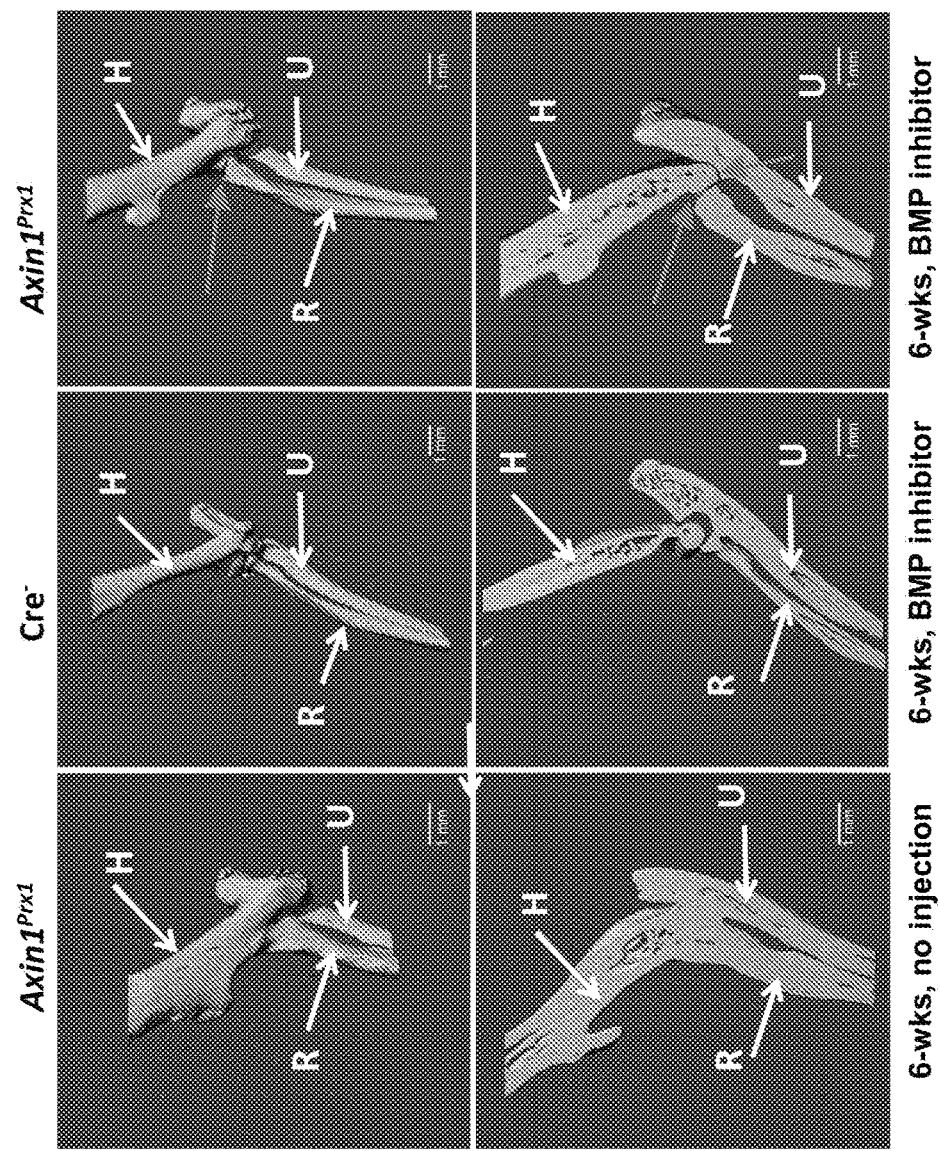
FIG. 24 shows inhibition of BMP signaling reversed elbow joint fusion phenotype in Axin1$^{Prx1}$ KO mice. BMP inhibitor, dorsomorphin, was given to pregnant mothers at E9.5 stage (2.5 mg/kg, i.p. injection, single dose). Micro-CT analysis of elbow joint of 6-week-old mice showed that humerus (H), radius (R) and ulna (U) are clearly separated in Axin1$^{Prx1}$ KO mice (right panel, red arrow) treated with dorsomorphin. No significant difference in the elbow joint was observed in Cre negative Axin1$^{flox/flox}$ mice treated with dorsomorphin compared to wild type mice.

Because it is well documented that BMP signaling acts on inhibition of synovial joint formation (Brunet et al., 1998, Tsumaki et al., 2002; Zou et al., 1997) and the Axin1$^{Prx1}$ mice and Axin1$^{Prx1}$/Axin2$^{+/-}$ mice showed multiple joint fusions involving humeroradial, carpal and tarsal joint that are very similar to those found noggin mutant mice, it is likely that BMP signaling pathway is one of those immediately downstream pathway of Axin1/β-catenin signaling during skeletal development. To test this possibility, we investigated if inhibition of BMP signaling will reverse skeletal defects of the Axin1$^{Prx1}$ mice. We injected Axin1$^{Prx1}$ mice intraperitoneally with BMP pathway inhibitor, dorsomorphin (2.5 mg/kg), which has recently been shown to inhibit BMPR-IA(ALK3), BMPR-IB (ALK6) and ALK2 activity (Yu et al., 2008), or vehicle at E9.5 stage. The embryos were collected at E18.5. Alcian blue/H&E staining on Axin1$^{Prx1}$ elbow joint sections at E18.5 revealed that the humerus, radius and ulna were clearly separated in Axin1$^{Prx1}$ KO treated with treatment of BMP inhibitor (FIG. 21). Dorsomorphin did not affect joint formation in the Cre negative embryos. These results demonstrated that the humeroradial and humeroulnar fusions in Axin1$^{Prx1}$ mice were rescued by blocking BMP signaling. Histologic examination of hindlimb sections of E18.5 embryos showed that fibular defects in Axin1$^{Prx1}$ embryos were significantly rescued by the treatment of dosomorphin (FIG. 22). In addition, BMP inhibitor dorsomorphin (2.5 mg/kg, i.p. injection, single dose) was injected into pregnant mothers at E9.5 stage. Micro-CT analysis of elbow joint of 6-week-old mice showed that the humerus (H), radius (R) and ulna (U) are clearly separated (FIG. 24, right panel, red arrow) in Axin1$^{Prx1}$ KO mice which were treated with dorsomorphin. And the fibular defect in Axin1$^{Prx1}$ mice was significantly also rescued by dosomorphin treatment (data not shown).

Figure 23:
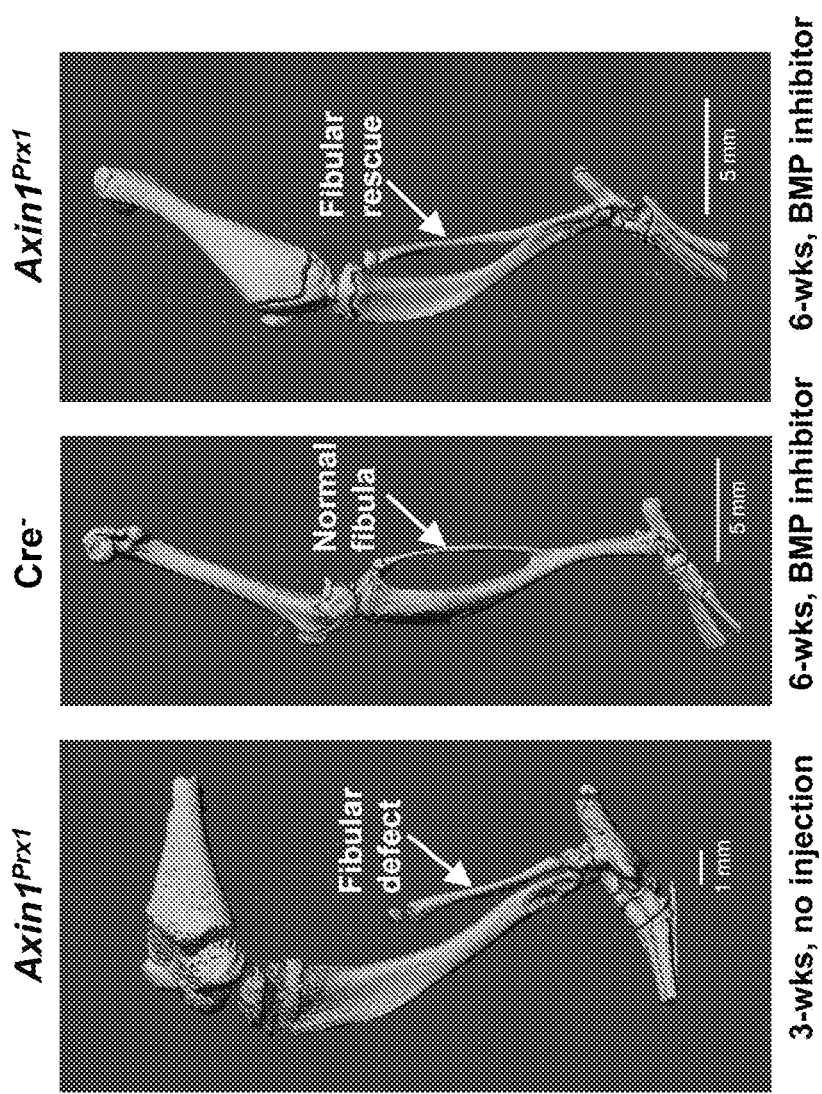
FIG. 23 shows inhibition of BMP signaling reversed fibular defects observed in Axin1$^{Prx1}$ KO mice. BMP inhibitor, dorsomorphin, was given to pregnant mothers at E13.5 stage (Axin1$^{Prx1}$ mice were bred with Axin1$^{flox/flox}$ mice) (5 mg/kg, i.p. injection, single dose). Administration of BMP inhibitor to Axin1$^{Prx1}$ KO mice almost completely reversed fibular defects observed in Axin1$^{Prx1}$ KO mice (right panel).

However, when we injected Axin1$^{Prx1}$ embryos with dorsomorphin (5 mg/kg) at E13.5 stage, the result of μCT analysis at 6 weeks of age showed that fibular defects in Axin1$^{Prx1}$ mice was significantly rescued by dosomorphin treatment (FIG. 23), but the elbow and tarsal joint fusions were still observed in the in Axin1$^{Prx1}$ mice (data not shown), suggesting that the timing for BMP inhibitor administration is very important. Taken together, these results indicate that BMP signaling pathway is a central downstream effector of Axin1/β-catenin signaling during skeletal development and the use of BMP inhibitor may represent a potential therapy for FH and HRS synostosis diseases.

Figure 25:
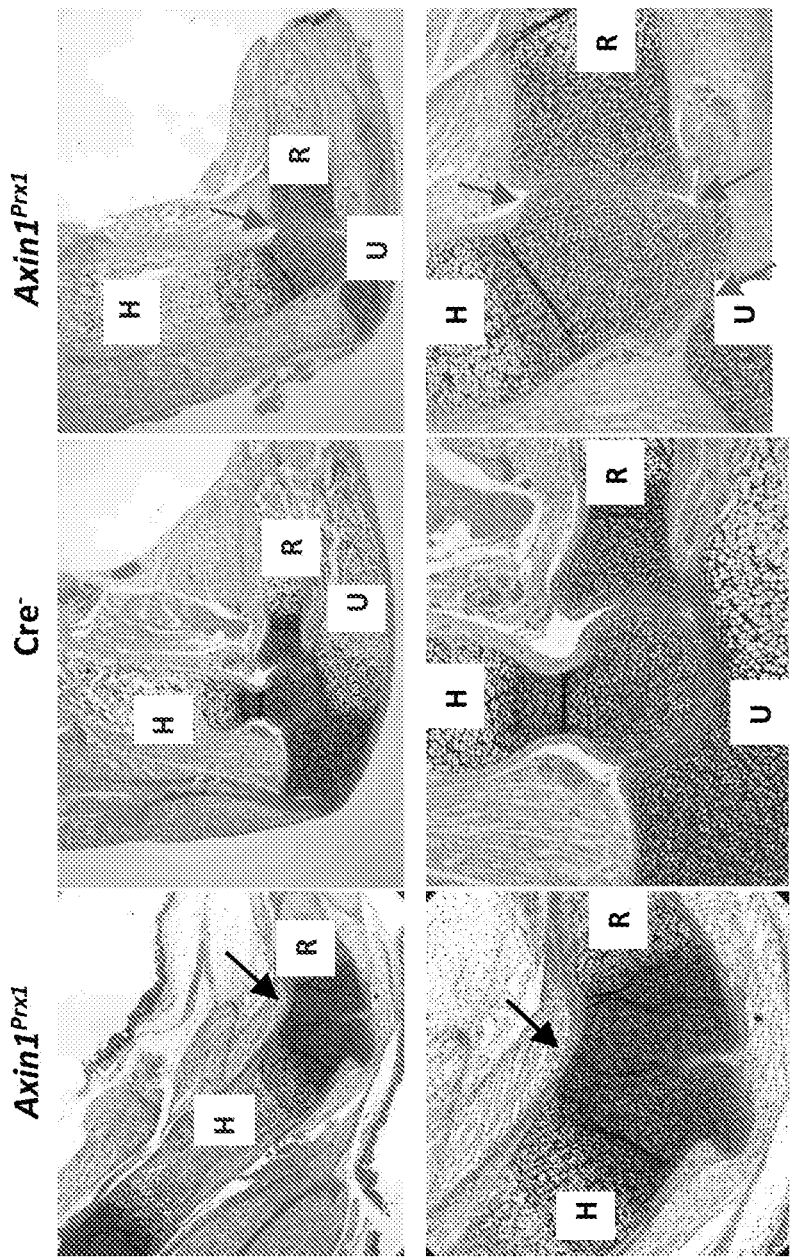
FIG. 25 shows inhibition of Wnt signaling reversed joint fusion phenotype of Axin1$^{Prx1}$ KO mice. Wnt inhibitor, iCRT14 (2.5 mg/kg, i.p. injection, single dose) was injected into pregnant mothers at E9.5 stage. Samples were collected at E18.5. Histological analysis showed that humerus (H), radius (R) and ulna (U) are clearly separated in Axin1$^{Prx1}$ mice (right panel, red arrow) treated with iCRT14. In contrast, histological sections of the elbow joint of E18.5 Axin1$^{Prx1}$ KO mice without treatment of Wnt inhibitor showed that humerus (H) and radius (R) were fused (left panel, black arrow). iCRT14 did not affect elbow joint formation in the Cre negative embryos (middle panel). Lower panels show higher magnification.

Example 6—Inhibition of Wnt Signaling Significantly Reversed FH and HRS Phenotypes Observed in Axin1$^{Prx1}$ Mice Our preliminary data demonstrated that deletion of one allele of β-catenin in Axin1$^{Prx1}$ mice significantly reversed FH and HRS phenotypes observed in in Axin1$^{Prx1}$ mice, suggesting that FH and HRS phenotypes observed in in Axin1$^{Prx1}$ mice are mediated by elevated Wnt/β-catenin level. To further determine the role of Wnt/β-catenin in skeletal development and to explore if Wnt inhibition could be used as a potential therapeutic treatment for FH/TC/HRS, Axin1$^{Prx1}$ mice (pregnant mother at E9.5 stage) were treated with the Wnt/β-catenin inhibitor, iCRT14 (inhibitor of β-catenin responsive transcription) (2.5 mg/kg, i.p. injection, single dose). iCRT14 is a small-molecule inhibitor of nuclear β-catenin function and has been shown to specifically inhibit Wnt/β-catenin-induced transcription by disrupting the interaction between β-catenin and TCF4 (Gonsalves et al. 2011). The embryos were collected at E18.5 stage. Histological analysis showed that the HRS phenotype in Axin1$^{Prx1}$ embryos was reversed. The humerus (H), radius (R) and ulna (U) are clearly separated (FIG. 25) in Axin1$^{Prx1}$ mice treated with iCRT14.

Figure 26:
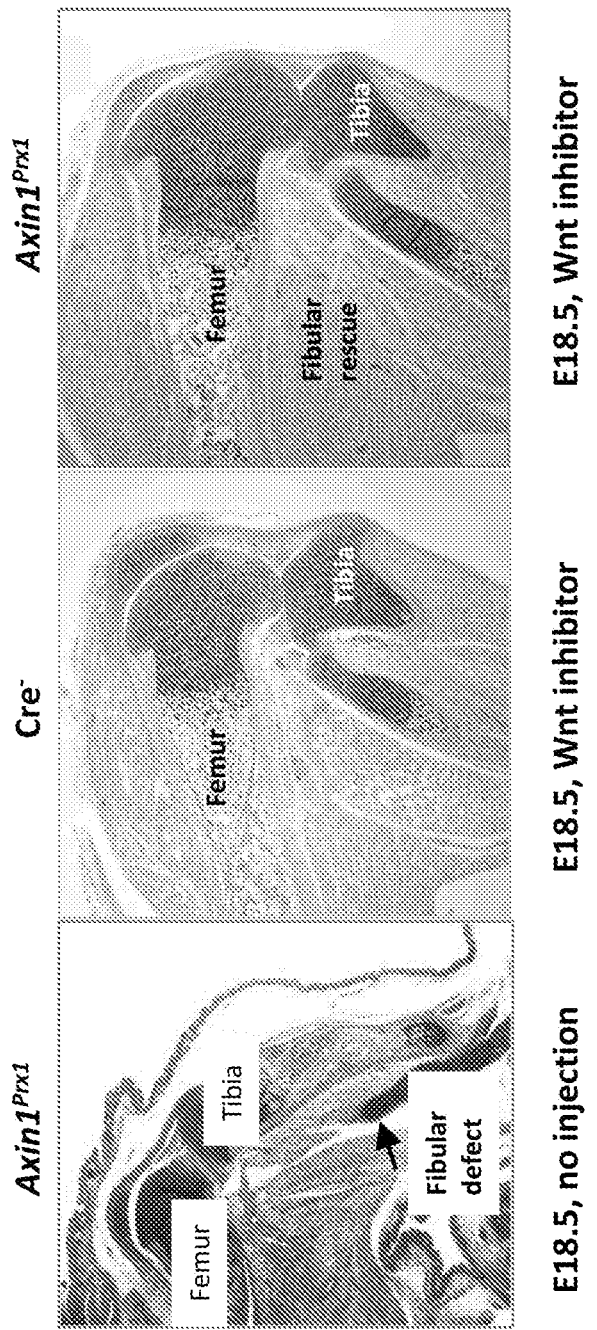
FIG. 26 shows inhibition of Wnt signaling reversed fibular defect observed in Axin1$^{Prx1}$ KO mice. Wnt inhibitor, iCRT14 (2.5 mg/kg, i.p. injection, single dose) was injected into pregnant mothers at E9.5 stage. Samples were collected at E18.5. Alcian Blue/Hematoxylin & Orange G staining of the hind limb of E18.5 Cre negative and Axin1$^{Prx1}$ KO mice showed that administration of Wnt inhibitor to Axin1$^{Prx1}$ mice significantly reversed fibular defect (right panel, green arrow) observed in Axin1$^{Prx1}$ KO mice.

A histological examination of hind limb section of E18.5 embryos showed that the fibular defects Axin1$^{Prx1}$ in mice were almost completely rescued by iCRT14 treatment (FIG. 26). iCRT14 did not affect joint formation and fibular development in the Cre negative embryos. These results demonstrate that β-catenin is a major signaling event downstream of canonical Wnt signaling, if not the only one. The results indicate that Wnt/β-catenin inhibitor represents a potential therapy for FH and HRS.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

REFERENCES

Achterman C, and Kalamchi A (1979) Congenital deficiency of the fibula, J Bone Joint Surg [Br] 61:133-7.

Brunet, L J, McMahon J A, McMahon A P, and Harland R M (1998) Noggin, cartilage morphogenesis, and joint formation in the mammalian skeleton. Science 280:1455-1457.

Coventry M B, and Johnson E W (1952) Congenital absence of fibula, J Bone Joint Surgery [Am] 34:941-55.

Chia I V, and Costantini F (2005) Mouse axin and axin2/conductin proteins are functionally equivalent in vivo. Mol Cell Biol 25: 4371-4376.

Chia I V, Kim M J, Itoh K, Sokol S Y, and Costantini F (2009) Both the RGS domain and the six C-terminal amino acids of mouse Axin are required for normal embryogenesis. Genetics 181:1359-1368.

Farley F W, Soriano P, Steffen L S, and Dymecki S M (2000) Widespread recombinase expression using FLPeR (Flipper) mice. Genesis 28:106-110.

Florio I, Wisser J, Huch R, and Huch A (1999) Prenatal ultrasound diagnosis of a femur-fibula-ulna complex during the first half of pregnancy. Fetal Diagn Ther 14:310-312.

Logan M, Martin J F, Nagy A, Lobe C, Olson E N, and Tabin C J (2002) Expression of Cre Recombinase in the developing mouse limb bud driven by a Prxl enhancer. Genesis 33:77-80.

Gillespie R, Torode I P. 1983 Classification and management of congenital abnormalities of the femur. J Bone Joint Burg (Br) 65(557-68).

Gonsalves, F. C., Klein, K., Carson, B. B., Katz, S., Ekas, L, A., Evans, S., Nagourney, R., Cardozo, T., Brown, A. M., DasGupta, R. 2011. An RNAi-based chemical genetic screen identifies three small-molecule inhibitors of the Wnt/wingless signaling pathway. Proc Natl Acad Sci USA 108: 5954-5963.

Kulik S A, Jr., Clanton T O 1996. Tarsal coalition. Foot & Ankle International 17(5): 286-96.

Ovchinnikov D A, Deng J M, Ogunrinu G, and Behringer R R (2000) Col2a1-directed expression of Cre recombinase in differentiating chondrocytes in transgenic mice. Genesis 26:145-146.

McIntyre J D, Benson M K. 2002. An aetiological classification for developmental Synostoses at the elbow, J Pediatr Orthop B. 11(4):313-319.

Perry W L III, Vasicek T J, Lee J J, Rossi J M, Zeng L, Zhang T, Tilghman S M, and Costantini F (1995) Phenotypic and molecular analysis of a transgenic insertional allele of the mouse Fused locus. Genetics 141:321-332.

Rodda, S J and McMahon A P (2006) Distinct roles for Hedgehog and canonical Wnt signaling in specification, differentiation and maintenance of osteoblast progenitors. Development 133:3231-3244.

Stanitski D F, and Stanitski C L (2003) Fibular hemimelia: A new classification system. J Pediatr Orthop 23: 30-34.

Thompson T C, Straub L R, and Arnold W D (1957) Congenital absence of the fibula. J Bone Joint Burg 39A, 1229-1237.

Tsumaki N, Tanaka K. Arikawa-Hirasewa E, Nakase T, Kimura T, Thomas J T, Ochi T, Luyten F P, and Yamada Y (1999) Role of CDMP-1 in skeletal morphogenesis: Promotion of mesenchymal cell recruitment and chondrocyte differentiation. J Cell Biol 144:161-173.

Xie R, Jiang R, and Chen D (2011) Generation of Axin1 conditional mutant mice. Genesis 9:98-102.

Yan Y, Tang D, Chen M, Huang J, Xie R, Jonason J H, Tan X, Hou W, Reynolds D, Hsu W, Harris S E, Puzas J E, Awad H, O'Keefe R J, Boyce B F, and Chen D (2009)

Axin2 controls bone remodeling through the (beta)-catenin-BMP signaling pathway in adult mice. J Cell Sci 122: 3566-3578.

Yu H M, Jerchow B, Sheu T J, Liu B, Costantini F, Puzas J E, Birchmeier W, and Hsu W (2005) The role of Axin2 in calvarial morphogenesis and craniosynostosis. Development 132:1995-2005.

Yu P B, Hong C C, Sachidanandan C, Babitt J L, Deng D Y, Hoyng S A, Lin H Y, Bloch K D, and Peterson R T (2008) Dorsomorphin inhibits BMP signals required for embryogenesis and iron metabolism. Nat Chem Biol 4:33-41.

Zeng L, Fagotto F, Zhang T, Hsu W, Vasicek T J, Perry W L 3rd, Lee J J, Tilghman S M, Gumbiner B M, and Costantini F (1997) The mouse Fused locus encodes Axin, an inhibitor of the Wnt signaling pathway that regulates embryonic axis formation. Cell 90:181-92.

Zou H, Weiser R, Massague J, and Niswander L (1997) Distinct roles of type I bone morphogenetic protein receptors in the formation and differentiation of cartilage. Genes Dev 11:2191-2203.

We claim:

1. A method for treating an orthopedic disease, comprising administering to a subject in need of such treatment a composition comprising a therapeutically effective amount of an inhibitor of beta-catenin signaling, wherein the orthopedic disease is fibular hemimelia.

2. The method of claim 1, wherein the composition is administered in-utero.

3. The method of claim 2, wherein the composition is administered in the third trimester of pregnancy.

4. The method of claim 1, wherein the composition is administered after birth of the subject.

5. The method of claim 1, wherein the subject is a subject having an elevated level of beta-catenin signaling.

6. The method of claim 1, wherein the inhibitor of beta-catenin signaling is selected from the group consisting of LGK-974, IWP-2, iCRT 3, iCRT 14, ICG 001, XAV-939, KY02111, and a combination of at least two thereof.

7. The method of claim 6, wherein the inhibitor of β-catenin signaling is iCRT 14.

8. The method of claim 6, wherein the inhibitor of β-catenin signaling is XAV-939.

9. The method of claim 6, wherein the inhibitor of β-catenin signaling is LGK-974.

10. The method of claim 6, wherein the inhibitor of β-catenin signaling is iCRT 3.

11. The method of claim 6, wherein the inhibitor of β-catenin signaling is IWP-2.

12. The method of claim 6, wherein the inhibitor of β-catenin signaling is ICG 001.

13. The method of claim 6, wherein the inhibitor of β-catenin signaling is KY02111.

* * * * *